United States Patent
Robbins et al.

(10) Patent No.: US 9,879,065 B2
(45) Date of Patent: Jan. 30, 2018

(54) T CELL RECEPTORS RECOGNIZING MHC CLASS II-RESTRICTED MAGE-A3

(71) Applicant: The United States of America, as represented by the Secretary, Department of Health and Human Services, Washington, DC (US)

(72) Inventors: Paul F. Robbins, Chevy Chase, MD (US); Steven A. Rosenberg, Potomac, MD (US); Xin Yao, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 88 days.

(21) Appl. No.: 14/427,671

(22) PCT Filed: Sep. 13, 2013

(86) PCT No.: PCT/US2013/059608
§ 371 (c)(1),
(2) Date: Mar. 12, 2015

(87) PCT Pub. No.: WO2014/043441
PCT Pub. Date: Mar. 20, 2014

(65) Prior Publication Data
US 2015/0246959 A1    Sep. 3, 2015

Related U.S. Application Data

(60) Provisional application No. 61/701,056, filed on Sep. 14, 2012.

(51) Int. Cl.
| A61K 39/395 | (2006.01) |
| C07K 14/725 | (2006.01) |
| A61K 38/17 | (2006.01) |
| C07K 14/73 | (2006.01) |
| A61K 39/00 | (2006.01) |
| C07K 16/00 | (2006.01) |
| C07K 16/28 | (2006.01) |
| G01N 33/574 | (2006.01) |

(52) U.S. Cl.
CPC ...... *C07K 14/7051* (2013.01); *A61K 38/1774* (2013.01); *A61K 39/0005* (2013.01); *C07K 14/70514* (2013.01); *C07K 16/00* (2013.01); *C07K 16/2809* (2013.01); *G01N 33/57492* (2013.01); *A61K 2039/585* (2013.01); *C07K 2319/00* (2013.01); *G01N 2333/47* (2013.01); *G01N 2333/7051* (2013.01)

(58) Field of Classification Search
None
See application file for complete search history.

(56) References Cited

U.S. PATENT DOCUMENTS

| 5,087,616 A | 2/1992 | Myers et al. |
| 5,225,539 A | 7/1993 | Winter |
| 5,449,752 A | 9/1995 | Fujii et al. |
| 5,545,806 A | 8/1996 | Lonberg et al. |
| 5,569,825 A | 10/1996 | Lonberg et al. |
| 5,585,089 A | 12/1996 | Queen et al. |
| 5,639,641 A | 6/1997 | Pedersen et al. |
| 5,693,761 A | 12/1997 | Queen et al. |
| 5,714,352 A | 2/1998 | Jakobovits |
| 6,265,150 B1 | 7/2001 | Terstappen et al. |
| 2002/0197266 A1 | 12/2002 | Debinski |

FOREIGN PATENT DOCUMENTS

| EP | 0 239 400 B1 | 8/1994 |
| GB | 2 188 638 A | 10/1987 |
| WO | WO 2012/013913 A1 | 2/2012 |
| WO | WO 2012/038055 A1 | 3/2012 |
| WO | WO 2012/054825 A1 | 4/2012 |
| WO | WO 2013/039889 A1 | 3/2013 |

OTHER PUBLICATIONS

Straetemans et al Clinical and Developmental Immunology 586314 p. 1 (2012).*
Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Strome et al., The Oncologist, 2007; 12:1084-95.*
Kataja et al., Ann Oncol 2009; 20(sup 4): iv10-14.*
Nelson et al., Ann. Intern Med. 2009; 151:727-737.*
Balmana et al. Ann Oncol 2009; 20(supp 4):iv19-20.*
Bonehill et al., "Messenger RNA-electroporated dendritic cells presenting MAGE-A3 simultaneously in HLA class I and class II molecules," *J. Immunol.*, 172 (11), 6649-6657 (2004).
Chinnasamy et al., "A TCR targeting the HLA-A*0201-restricted epitope of MAGE-A3 recognizes multiple epitopes of the MAGE-A antigen superfamily in several types of cancer," *J. Immunol.*, 186 (2), 685-696 (2011), e-published 2010.
Choi et al., "Synthesis and assembly of a cholera toxin B subunit-rotavirus VP7 fusion protein in transgenic potato," *Mol. Biotechnol.*, 31 (3), 193-202 (2005).
François et al., "The CD4(+) T-cell response of melanoma patients to a MAGE-A3 peptide vaccine involves potential regulatory T cells," *Cancer Res.*, 69 (10), 4335-4345 (2009).

(Continued)

*Primary Examiner* — Sheela J. Huff
(74) *Attorney, Agent, or Firm* — Leydig, Voit & Mayer

(57) ABSTRACT

The invention provides an isolated or purified T-cell receptor (TCR) having antigenic specificity for MHC Class II-restricted MAGE-A3. The invention further provides related polypeptides and proteins, as well as related nucleic acids, recombinant expression vectors, host cells, and populations of cells. Further provided by the invention are antibodies, or an antigen binding portion thereof, and pharmaceutical compositions relating to the TCRs of the invention. Methods of detecting the presence of cancer in a host and methods of treating or preventing cancer in a mammal are further provided by the invention.

35 Claims, 10 Drawing Sheets

(56) References Cited

OTHER PUBLICATIONS

Genbank Accession No. ACA28841.1 (printed Mar. 1, 2008).
Genbank Accession No. ACA28842.1 (printed Mar. 1, 2008).
Genbank Accession No. EU427376.1 (printed Mar. 1, 2008).
Genbank Accession No. EU427377.1 (printed Mar. 1, 2008).
Haskard et al., "The production of human monoclonal autoantibodies from patients with rheumatoid arthritis by the EBV-hybridoma technique," *J. Immunol. Methods*, 74 (2), 361-367 (1984).
Hudecz, "Synthesis of peptide bioconjugates," *Methods Mol. Biol.*, 298, 209-223 (2005).
Huse et al., "Generation of a large combinatorial library of the immunoglobulin repertoire in phage lambda," *Science*, 246 (4935), 1275-1281 (1989).
International Preliminary Report on Patentability, Application No. PCT/US2013/059608, dated Mar. 17, 2015.
International Search Report, Application No. PCT/US2013/059608, dated Nov. 12, 2013.
Karanikas et al., "Monoclonal anti-MAGE-3 CTL responses in melanoma patients displaying tumor regression after vaccination with a recombinant canarypox virus," *J. Immunol.*, 171 (9), 4898-4904 (2003).
Kirin et al., "Amino acid and peptide bioconjugates of copper(II) and zinc(II) complexes with a modified N,N-bis(2-picolyl)amine ligand," *Inorg. Chem.*, 44 (15), 5405-5415 (2005).
Köhler et al., "Derivation of specific antibody-producing tissue culture and tumor lines by cell fusion," *Eur. J. Immunol.*, 6 (7), 511-519 (1976).
Pedersen et al., "Comparison of surface accessible residues in human and murine immunoglobulin Fv domains. Implication for humanization of murine antibodies," *J. Mol. Biol.*, 235 (3), 959-973 (1994).
Reiter et al., "Engineering interchain disulfide bonds into conserved framework regions of Fv fragments: improved biochemical characteristics of recombinant immunotoxins containing disulfide-stabilized Fv," *Protein Eng.*, 7 (5), 697-704 (1994).
Roder et al., "The EBV-hybridoma technique," *Methods Enzymol.*, 121, 140-167 (1986).
Schultz et al., "Functional analysis of tumor-specific Th cell responses detected in melanoma patients after dendritic cell-based immunotherapy," *J. Immunol.*, 172 (2), 1304-1310 (2004).
Straetemans et al., "TCR gene transfer: MAGE-C2/HLA-A2 and MAGE-A3/HLA-DP4 epitopes as melanoma-specific immune targets," *Clin. Dev. Immunol., 586314*, 1-14 (2012), e-published Feb. 12, 2012.
Wadwa et al., "J. Drug Targeting, Receptor mediated glycotargeting," J. Drug Target., 3 (2), 111-127 (1995).
Written Opinion of the International Searching Authority, Application No. PCT/US2013/059608, dated Nov. 12, 2013.
6F9 TCR current clinical trial data as of Apr. 11, 2017.
"TRA T-cell receptor alpha locus [Homo sapiens (human)]," Gene ID: 6955, (updated Oct. 9, 2016), Entrez Gene (mvw.ncbi.nim.nih.gov/gene), printed on Dec. 8, 2016.
"TRB T cell receptor beta locus [Homo sapiens (human)]," Gene ID: 6957, (updated Oct. 9, 2016), Entrez Gene (www.ncbi.nlm.nih.gov/gene), printed on Dec. 8, 2016.
Yao et al., "Isolation and Characterization of an HLA-DPB1*04:01-restricted MAGE-A3 T-Cell Receptor for Cancer Immunotherapy," *Immunotherapy Journal*, 39(5); 191-201 (2016).

* cited by examiner

SEQUENCE LISTING

```
<160> NUMBER OF SEQ ID NOS: 71

<210> SEQ ID NO 1
<211> LENGTH: 314
<212> TYPE: PRT
<213> ORGANISM: Homo sapiens

<400> SEQUENCE: 1

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255
```

-continued

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310

<210> SEQ ID NO 2
<211> LENGTH: 16
<212> TYPE: PRT
<213> ORGANISM: Homo sapiens

<400> SEQUENCE: 2

Lys Lys Leu Leu Thr Gln His Phe Val Gln Glu Asn Tyr Leu Glu Tyr
1               5                   10                  15

<210> SEQ ID NO 3
<211> LENGTH: 7
<212> TYPE: PRT
<213> ORGANISM: Homo sapiens

<400> SEQUENCE: 3

Thr Ser Glu Ser Asp Tyr Tyr
1               5

<210> SEQ ID NO 4
<211> LENGTH: 7
<212> TYPE: PRT
<213> ORGANISM: Homo sapiens

<400> SEQUENCE: 4

Gln Glu Ala Tyr Lys Gln Gln
1               5

<210> SEQ ID NO 5
<211> LENGTH: 11
<212> TYPE: PRT
<213> ORGANISM: Homo sapiens

<400> SEQUENCE: 5

Ala Leu Arg Ser Ser Gly Thr Tyr Lys Tyr Ile
1               5                   10

<210> SEQ ID NO 6
<211> LENGTH: 5
<212> TYPE: PRT
<213> ORGANISM: Homo sapiens

<400> SEQUENCE: 6

Ser Gly His Thr Ala
1               5

<210> SEQ ID NO 7
<211> LENGTH: 6
<212> TYPE: PRT
<213> ORGANISM: Homo sapiens

<400> SEQUENCE: 7

Phe Gln Gly Asn Ser Ala
1               5

<210> SEQ ID NO 8
<211> LENGTH: 15
<212> TYPE: PRT
<213> ORGANISM: Homo sapiens

<400> SEQUENCE: 8

```
Ala Ser Ile Arg Thr Gly Pro Phe Phe Ser Gly Asn Thr Ile Tyr
1               5                   10                  15
```

<210> SEQ ID NO 9
<211> LENGTH: 134
<212> TYPE: PRT
<213> ORGANISM: Homo sapiens

<400> SEQUENCE: 9

```
Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Ser Asp Tyr Tyr Leu Phe Trp Tyr Lys Gln Pro Pro Ser Arg Gln
        50                  55                  60

Met Ile Leu Val Ile Arg Gln Glu Ala Tyr Lys Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Leu Arg Ser Ser Gly Thr Tyr Lys Tyr Ile Phe Gly Thr Gly Thr
        115                 120                 125

Arg Leu Lys Val Leu Ala
    130
```

<210> SEQ ID NO 10
<211> LENGTH: 137
<212> TYPE: PRT
<213> ORGANISM: Homo sapiens

<400> SEQUENCE: 10

```
Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
                20                  25                  30

Glu Lys Gly Lys Asp Val Glu Leu Arg Cys Asp Pro Ile Ser Gly His
            35                  40                  45

Thr Ala Leu Tyr Trp Tyr Arg Gln Ser Leu Gly Gln Gly Leu Glu Phe
        50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ile Arg Thr Gly Pro Phe Phe Ser Gly Asn Thr Ile Tyr Phe Gly
        115                 120                 125

Glu Gly Ser Trp Leu Thr Val Val Glu
    130                 135
```

```
<210> SEQ ID NO 11
<211> LENGTH: 275
<212> TYPE: PRT
<213> ORGANISM: Homo sapiens

<400> SEQUENCE: 11

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Leu Arg Ser Ser Gly Thr Tyr Lys Tyr Ile Phe Gly Thr Gly Thr
        115                 120                 125

Arg Leu Lys Val Leu Ala Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 12
<211> LENGTH: 313
<212> TYPE: PRT
<213> ORGANISM: Homo sapiens

<400> SEQUENCE: 12

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45
```

-continued

Thr Ala Leu Tyr Trp Tyr Arg Gln Ser Leu Gly Gln Gly Leu Glu Phe
        50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ile Arg Thr Gly Pro Phe Phe Ser Gly Asn Thr Ile Tyr Phe Gly
            115                 120                 125

Glu Gly Ser Trp Leu Thr Val Val Glu Asp Leu Asn Lys Val Phe Pro
        130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Phe Pro Asp His
                165                 170                 175

Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
        195                 200                 205

Arg Tyr Cys Leu Ser Ser Arg Leu Arg Val Ser Ala Thr Phe Trp Gln
210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Val
            260                 265                 270

Ser Tyr Gln Gln Gly Val Leu Ser Ala Thr Ile Leu Tyr Glu Ile Leu
        275                 280                 285

Leu Gly Lys Ala Thr Leu Tyr Ala Val Leu Val Ser Ala Leu Val Leu
290                 295                 300

Met Ala Met Val Lys Arg Lys Asp Phe
305                 310

<210> SEQ ID NO 13
<211> LENGTH: 7
<212> TYPE: PRT
<213> ORGANISM: Homo sapiens

<400> SEQUENCE: 13

Thr Ser Glu Ser Asp Tyr Tyr
1               5

<210> SEQ ID NO 14
<211> LENGTH: 7
<212> TYPE: PRT
<213> ORGANISM: Homo sapiens

<400> SEQUENCE: 14

Gln Glu Ala Tyr Lys Gln Gln
1               5

<210> SEQ ID NO 15
<211> LENGTH: 17
<212> TYPE: PRT
<213> ORGANISM: Homo sapiens

```
<400> SEQUENCE: 15

Ala Tyr Thr Val Pro Ser Asn Ala Gly Gly Thr Ser Tyr Gly Lys Leu
1               5                   10                  15

Thr

<210> SEQ ID NO 16
<211> LENGTH: 5
<212> TYPE: PRT
<213> ORGANISM: Homo sapiens

<400> SEQUENCE: 16

Ser Asn His Leu Tyr
1               5

<210> SEQ ID NO 17
<211> LENGTH: 6
<212> TYPE: PRT
<213> ORGANISM: Homo sapiens

<400> SEQUENCE: 17

Phe Tyr Asn Asn Glu Ile
1               5

<210> SEQ ID NO 18
<211> LENGTH: 12
<212> TYPE: PRT
<213> ORGANISM: Homo sapiens

<400> SEQUENCE: 18

Ala Ser Ser Glu Arg Gly Gln Gly Tyr Gly Tyr Thr
1               5                   10

<210> SEQ ID NO 19
<211> LENGTH: 140
<212> TYPE: PRT
<213> ORGANISM: Homo sapiens

<400> SEQUENCE: 19

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Ser Asp Tyr Tyr Leu Phe Trp Tyr Lys Gln Pro Pro Ser Arg Gln
        50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
                100                 105                 110

Ala Tyr Thr Val Pro Ser Asn Ala Gly Gly Thr Ser Tyr Gly Lys Leu
            115                 120                 125

Thr Phe Gly Gln Gly Thr Ile Leu Thr Val His Pro
        130                 135                 140
```

-continued

```
<210> SEQ ID NO 20
<211> LENGTH: 134
<212> TYPE: PRT
<213> ORGANISM: Homo sapiens

<400> SEQUENCE: 20

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Arg Gly Gly Tyr Gly Tyr Thr Phe Gly Ser Gly Thr
        115                 120                 125

Arg Leu Thr Val Val Glu
    130

<210> SEQ ID NO 21
<211> LENGTH: 281
<212> TYPE: PRT
<213> ORGANISM: Homo sapiens

<400> SEQUENCE: 21

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Thr Val Pro Ser Asn Ala Gly Gly Thr Ser Tyr Gly Lys Leu
        115                 120                 125

Thr Phe Gly Gln Gly Thr Ile Leu Thr Val His Pro Asn Ile Gln Asn
    130                 135                 140

Pro Asp Pro Ala Val Tyr Gln Leu Arg Asp Ser Lys Ser Ser Asp Lys
145                 150                 155                 160

Ser Val Cys Leu Phe Thr Asp Phe Asp Ser Gln Thr Asn Val Ser Gln
                165                 170                 175

Ser Lys Asp Ser Asp Val Tyr Ile Thr Asp Lys Thr Val Leu Asp Met
            180                 185                 190
```

```
Arg Ser Met Asp Phe Lys Ser Asn Ser Ala Val Ala Trp Ser Asn Lys
        195                 200                 205

Ser Asp Phe Ala Cys Ala Asn Ala Phe Asn Asn Ser Ile Ile Pro Glu
210                 215                 220

Asp Thr Phe Phe Pro Ser Pro Glu Ser Ser Cys Asp Val Lys Leu Val
225                 230                 235                 240

Glu Lys Ser Phe Glu Thr Asp Thr Asn Leu Asn Phe Gln Asn Leu Ser
            245                 250                 255

Val Ile Gly Phe Arg Ile Leu Leu Lys Val Ala Gly Phe Asn Leu
            260                 265                 270

Leu Met Thr Leu Arg Leu Trp Ser Ser
            275                 280

<210> SEQ ID NO 22
<211> LENGTH: 310
<212> TYPE: PRT
<213> ORGANISM: Homo sapiens

<400> SEQUENCE: 22

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Arg Gly Gln Gly Tyr Gly Tyr Thr Phe Gly Ser Gly Thr
        115                 120                 125

Arg Leu Thr Val Val Glu Asp Leu Asn Lys Val Phe Pro Pro Glu Val
130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285
```

```
Ala Thr Leu Tyr Ala Val Leu Val Ser Ala Leu Val Leu Met Ala Met
    290                 295                 300

Val Lys Arg Lys Asp Phe
305                 310

<210> SEQ ID NO 23
<211> LENGTH: 141
<212> TYPE: PRT
<213> ORGANISM: Homo sapiens

<400> SEQUENCE: 23

Asn Ile Gln Asn Pro Asp Pro Ala Val Tyr Gln Leu Arg Asp Ser Lys
1               5                  10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
        50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 24
<211> LENGTH: 176
<212> TYPE: PRT
<213> ORGANISM: Homo sapiens

<400> SEQUENCE: 24

Asp Leu Asn Lys Val Phe Pro Pro Glu Val Ala Val Phe Glu Pro Ser
1               5                  10                  15

Glu Ala Glu Ile Ser His Thr Gln Lys Ala Thr Leu Val Cys Leu Ala
                20                  25                  30

Thr Gly Phe Phe Pro Asp His Val Glu Leu Ser Trp Trp Val Asn Gly
            35                  40                  45

Lys Glu Val His Ser Gly Val Ser Thr Asp Pro Gln Pro Leu Lys Glu
        50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Val Ser Tyr Gln Gln Gly Val Leu Ser Ala
    130                 135                 140
```

```
Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Phe
                165                 170                 175

<210> SEQ ID NO 25
<211> LENGTH: 137
<212> TYPE: PRT
<213> ORGANISM: Mus musculus

<400> SEQUENCE: 25

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
                20                  25                  30

Asn Val Pro Lys Thr Met Glu Ser Gly Thr Phe Ile Thr Asp Lys Thr
            35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135

<210> SEQ ID NO 26
<211> LENGTH: 172
<212> TYPE: PRT
<213> ORGANISM: Mus musculus

<400> SEQUENCE: 26

Asp Leu Arg Asn Val Thr Pro Pro Lys Val Ser Leu Phe Glu Pro Ser
1               5                   10                  15

Lys Ala Glu Ile Ala Asn Lys Gln Lys Ala Thr Leu Val Cys Leu Ala
                20                  25                  30

Arg Gly Phe Phe Pro Asp His Val Glu Leu Ser Trp Trp Val Asn Gly
            35                  40                  45

Lys Glu Val His Ser Gly Val Ser Thr Asp Pro Gln Ala Tyr Lys Glu
    50                  55                  60

Ser Asn Tyr Ser Tyr Cys Leu Ser Ser Arg Leu Arg Val Ser Ala Thr
65                  70                  75                  80

Phe Trp His Asn Pro Arg Asn His Phe Arg Cys Gln Val Gln Phe His
                85                  90                  95

Gly Leu Ser Glu Glu Asp Lys Trp Pro Glu Gly Ser Pro Lys Pro Val
            100                 105                 110

Thr Gln Asn Ile Ser Ala Glu Ala Trp Gly Arg Ala Asp Cys Gly Ile
        115                 120                 125

Thr Ser Ala Ser Tyr His Gln Gly Val Leu Ser Ala Thr Ile Leu Tyr
    130                 135                 140
```

Glu Ile Leu Leu Gly Lys Ala Thr Leu Tyr Ala Val Leu Val Ser Gly
145                 150                 155                 160

Leu Val Leu Met Ala Met Val Lys Arg Lys Asn Ser
                165                 170

<210> SEQ ID NO 27
<211> LENGTH: 271
<212> TYPE: PRT
<213> ORGANISM: Artificial Sequence
<220> FEATURE:
<223> OTHER INFORMATION: Synthetic

<400> SEQUENCE: 27

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Ser Asp Tyr Tyr Leu Phe Trp Tyr Lys Gln Pro Pro Ser Arg Gln
        50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
                100                 105                 110

Ala Leu Arg Ser Ser Gly Thr Tyr Lys Tyr Ile Phe Gly Thr Gly Thr
            115                 120                 125

Arg Leu Lys Val Leu Ala Asn Ile Gln Asn Pro Glu Pro Ala Val Tyr
        130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Thr Val Leu Asp Met Lys Ala Met Asp Ser Lys
                180                 185                 190

Ser Asn Gly Ala Ile Ala Trp Ser Asn Gln Thr Ser Phe Thr Cys Gln
            195                 200                 205

Asp Ile Phe Lys Glu Thr Asn Ala Thr Tyr Pro Ser Ser Asp Val Pro
        210                 215                 220

Cys Asp Ala Thr Leu Thr Glu Lys Ser Phe Glu Thr Asp Met Asn Leu
225                 230                 235                 240

Asn Phe Gln Asn Leu Ser Val Met Gly Leu Arg Ile Leu Leu Leu Lys
                245                 250                 255

Val Ala Gly Phe Asn Leu Leu Met Thr Leu Arg Leu Trp Ser Ser
                260                 265                 270

<210> SEQ ID NO 28
<211> LENGTH: 309
<212> TYPE: PRT
<213> ORGANISM: Artificial Sequence
<220> FEATURE:
<223> OTHER INFORMATION: Synthetic

```
<400> SEQUENCE: 28

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ile Arg Thr Gly Pro Phe Phe Ser Gly Asn Thr Ile Tyr Phe Gly
        115                 120                 125

Glu Gly Ser Trp Leu Thr Val Val Glu Asp Leu Arg Asn Val Thr Pro
    130                 135                 140

Pro Lys Val Ser Leu Phe Glu Pro Ser Lys Ala Glu Ile Ala Asn Lys
145                 150                 155                 160

Gln Lys Ala Thr Leu Val Cys Leu Ala Arg Gly Phe Phe Pro Asp His
                165                 170                 175

Val Glu Leu Ser Trp Trp Val Asn Gly Lys Glu Val His Ser Gly Val
            180                 185                 190

Ser Thr Asp Pro Gln Ala Tyr Lys Glu Ser Asn Tyr Ser Tyr Cys Leu
        195                 200                 205

Ser Ser Arg Leu Arg Val Ser Ala Thr Phe Trp His Asn Pro Arg Asn
    210                 215                 220

His Phe Arg Cys Gln Val Gln Phe His Gly Leu Ser Glu Glu Asp Lys
225                 230                 235                 240

Trp Pro Glu Gly Ser Pro Lys Pro Val Thr Gln Asn Ile Ser Ala Glu
                245                 250                 255

Ala Trp Gly Arg Ala Asp Cys Gly Ile Thr Ser Ala Ser Tyr His Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Gly Leu Val Leu Met Ala Met Val
    290                 295                 300

Lys Arg Lys Asn Ser
305

<210> SEQ ID NO 29
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(5)
<223> OTHER INFORMATION: X at 4 and 5 is Ser, Ala, Leu, Ile, Val, or Met
<220> FEATURE:
<221> NAME/KEY: MISC_FEATURE
<222> LOCATION: (6)..(6)
<223> OTHER INFORMATION: X at 6 is Gly, Ala, Leu, Ile, Val, or Met
```

```
<220> FEATURE:
<221> NAME/KEY: MISC_FEATURE
<222> LOCATION: (7)..(7)
<223> OTHER INFORMATION: X at 7 is Thr, Ala, Leu, Ile, Val, or Met
<220> FEATURE:
<221> NAME/KEY: MISC_FEATURE
<222> LOCATION: (7)..(7)
<223> OTHER INFORMATION: X at 7 is Thr, Ala, Leu, Ile, Val, or Met

<400> SEQUENCE: 29

Ala Leu Arg Xaa Xaa Xaa Xaa Tyr Lys Tyr Ile
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X at 4 is Arg, Ala, Leu, Ile, Val, or Met
<220> FEATURE:
<221> NAME/KEY: MISC_FEATURE
<222> LOCATION: (5)..(5)
<223> OTHER INFORMATION: X at 5 is Thr, Ala, Leu, Ile, Val, or Met
<220> FEATURE:
<221> NAME/KEY: MISC_FEATURE
<222> LOCATION: (6)..(6)
<223> OTHER INFORMATION: X at 6 is Gly, Ala, Leu, Ile, Val, or Met
<220> FEATURE:
<221> NAME/KEY: MISC_FEATURE
<222> LOCATION: (7)..(7)
<223> OTHER INFORMATION: X at 7 is Pro, Ala, Leu, Ile, Val, or Met

<400> SEQUENCE: 30

Ala Ser Ile Xaa Xaa Xaa Xaa Phe Phe Ser Gly Asn Thr Ile Tyr
1               5                   10                  15

<210> SEQ ID NO 31
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (116)..(117)
<220> FEATURE:
<221> NAME/KEY: MISC_FEATURE
<222> LOCATION: (116)..(117)
<220> FEATURE:
<221> NAME/KEY: MISC_FEATURE
<222> LOCATION: (118)..(118)
<220> FEATURE:
<221> NAME/KEY: MISC_FEATURE
<222> LOCATION: (119)..(119)

<400> SEQUENCE: 31

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
                20                  25                  30

Val Gln Glu Ala Glu Thr Val Thr Leu Ser Cys Thr Tyr Asp Thr Ser
            35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80
```

```
Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Leu Arg Xaa Xaa Xaa Xaa Tyr Lys Tyr Ile Phe Gly Thr Gly Thr
        115                 120                 125

Arg Leu Lys Val Leu Ala
    130
```

```
<210> SEQ ID NO 32
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (115)..(115)
<223> OTHER INFORMATION: X at 115 is Arg, Ala, Leu, Ile, Val, or Met
<220> FEATURE:
<221> NAME/KEY: misc_feature
<222> LOCATION: (116)..(116)
<223> OTHER INFORMATION: X at 116 is Thr, Ala, Leu, Ile, Val, or Met
<220> FEATURE:
<221> NAME/KEY: misc_feature
<222> LOCATION: (117)..(117)
<223> OTHER INFORMATION: X at 117 is Gly, Ala, Leu, Ile, Val, or Met
<220> FEATURE:
<221> NAME/KEY: misc_feature
<222> LOCATION: (118)..(118)
<223> OTHER INFORMATION: X at 118 is Pro, Ala, Leu, Ile, Val, or Met

<400> SEQUENCE: 32
```

```
Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ile Xaa Xaa Xaa Xaa Phe Phe Ser Gly Asn Thr Ile Tyr Phe Gly
        115                 120                 125

Glu Gly Ser Trp Leu Thr Val Val Glu
    130                 135
```

```
<210> SEQ ID NO 33
<211> LENGTH: 275
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (116)..(117)
<223> OTHER INFORMATION: X at 116 and 117 is Ser, Ala, Leu, Ile, Val, or
      Met
```

```
<220> FEATURE:
<221> NAME/KEY: MISC_FEATURE
<222> LOCATION: (118)..(118)
<223> OTHER INFORMATION: X at 118 is Gly, Ala, Leu, Ile, Val, or Met
<220> FEATURE:
<221> NAME/KEY: MISC_FEATURE
<222> LOCATION: (119)..(119)
<223> OTHER INFORMATION: X at 119 is Thr, Ala, Leu, Ile, Val, or Met

<400> SEQUENCE: 33

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Leu Arg Xaa Xaa Xaa Xaa Tyr Lys Tyr Ile Phe Gly Thr Gly Thr
        115                 120                 125

Arg Leu Lys Val Leu Ala Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 34
<211> LENGTH: 313
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (115)..(115)
<223> OTHER INFORMATION: X at 115 is Arg, Ala, Leu, Ile, Val, or Met
```

```
<220> FEATURE:
<221> NAME/KEY: MISC_FEATURE
<222> LOCATION: (116)..(116)
<223> OTHER INFORMATION: X at 116 is Thr, Ala, Leu, Ile, Val, or Met
<220> FEATURE:
<221> NAME/KEY: MISC_FEATURE
<222> LOCATION: (117)..(117)
<223> OTHER INFORMATION: X at 117 is Gly, Ala, Leu, Ile, Val, or Met
<220> FEATURE:
<221> NAME/KEY: MISC_FEATURE
<222> LOCATION: (118)..(118)
<223> OTHER INFORMATION: X at 118 is Pro, Ala, Leu, Ile, Val, or Met

<400> SEQUENCE: 34

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ile Xaa Xaa Xaa Xaa Phe Phe Ser Gly Asn Thr Ile Tyr Phe Gly
        115                 120                 125

Glu Gly Ser Trp Leu Thr Val Val Glu Asp Leu Asn Lys Val Phe Pro
    130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Phe Pro Asp His
                165                 170                 175

Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
        195                 200                 205

Arg Tyr Cys Leu Ser Ser Arg Leu Arg Val Ser Ala Thr Phe Trp Gln
    210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Val
            260                 265                 270

Ser Tyr Gln Gln Gly Val Leu Ser Ala Thr Ile Leu Tyr Glu Ile Leu
        275                 280                 285

Leu Gly Lys Ala Thr Leu Tyr Ala Val Leu Val Ser Ala Leu Val Leu
    290                 295                 300

Met Ala Met Val Lys Arg Lys Asp Phe
305                 310
```

<210> SEQ ID NO 35
<211> LENGTH: 141
<212> TYPE: PRT
<213> ORGANISM: Homo sapiens

<400> SEQUENCE: 35

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 36
<211> LENGTH: 176
<212> TYPE: PRT
<213> ORGANISM: Homo sapiens

<400> SEQUENCE: 36

Asp Leu Asn Lys Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Phe Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Val Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Phe
                165                 170                 175

<210> SEQ ID NO 37
<211> LENGTH: 828
<212> TYPE: DNA
<213> ORGANISM: Homo sapiens

<400> SEQUENCE: 37

| | | | | | |
|---|---|---|---|---|---|
| atggcatgcc | ctggcttcct | gtgggcactt | gtgatctcca | cctgtcttga | atttagcatg | 60 |
| gctcagacag | tcactcagtc | tcaaccagag | atgtctgtgc | aggaggcaga | gaccgtgacc | 120 |
| ctgagctgca | catatgacac | cagtgagagt | gattattatt | tattctggta | caagcagcct | 180 |
| cccagcaggc | agatgattct | cgttattcgc | caagaagctt | ataagcaaca | gaatgcaaca | 240 |
| gagaatcgtt | tctctgtgaa | cttccagaaa | gcagccaaat | ccttcagtct | caagatctca | 300 |
| gactcacagc | tgggggatgc | cgcgatgtat | ttctgtgctc | tccggagctc | aggaacctac | 360 |
| aaatacatct | ttggaacagg | caccaggctg | aaggttttag | caaatatcca | gaaccctgac | 420 |
| cctgccgtgt | accagctgag | agactctaaa | tccagtgaca | agtctgtctg | cctattcacc | 480 |
| gattttgatt | ctcaaacaaa | tgtgtcacaa | gtaaggatt | ctgatgtgta | tatcacagac | 540 |
| aaaactgtgc | tagacatgag | gtctatggac | ttcaagagca | acagtgctgt | ggcctggagc | 600 |
| aacaaatctg | actttgcatg | tgcaaacgcc | ttcaacaaca | gcattattcc | agaagacacc | 660 |
| ttcttcccca | gcccagaaag | ttcctgtgat | gtcaagctgg | tcgagaaaag | ctttgaaaca | 720 |
| gatacgaacc | taaactttca | aaacctgtca | gtgattgggt | tccgaatcct | cctcctgaaa | 780 |
| gtggccgggt | ttaatctgct | catgacgctg | cggctgtggt | ccagctga | | 828 |

<210> SEQ ID NO 38
<211> LENGTH: 942
<212> TYPE: DNA
<213> ORGANISM: Homo sapiens

<400> SEQUENCE: 38

| | | | | | |
|---|---|---|---|---|---|
| atgggcacca | ggctcctctt | ctgggtggcc | ttctgtctcc | tgggggcaga | tcacacagga | 60 |
| gctggagtct | cccagtcccc | cagtaacaag | gtcacagaga | agggaaagga | tgtagagctc | 120 |
| aggtgtgatc | caatttcagg | tcatactgcc | ctttactggt | accgacagag | cctggggcag | 180 |
| ggcctggagt | ttttaattta | cttccaaggc | aacagtgcac | cagacaaatc | agggctgccc | 240 |
| agtgatcgct | tctctgcaga | gaggactggg | ggatccgtct | ccactctgac | gatccagcgc | 300 |
| acacagcagg | aggactcggc | cgtgtatctc | tgtgccagca | tccggacagg | gcctttttc | 360 |
| tctggaaaca | ccatatattt | tggagaggga | agttggctca | ctgttgtaga | ggacctgaac | 420 |
| aaggtgttcc | cacccgaggt | cgctgtgttt | gagccatcag | aagcagagat | ctcccacacc | 480 |
| caaaaggcca | cactggtgtg | cctggccaca | ggcttcttcc | ctgaccacgt | ggagctgagc | 540 |
| tggtgggtga | atgggaagga | ggtgcacagt | ggggtcagca | cggacccgca | gccccctcaag | 600 |
| gagcagcccg | ccctcaatga | ctccagatac | tgcctgagca | gccgcctgag | ggtctcggcc | 660 |
| accttctggc | agaaccccccg | caaccacttc | cgctgtcaag | tccagttcta | cgggctctcg | 720 |
| gagaatgacg | agtggaccca | ggataggggcc | aaacccgtca | cccagatcgt | cagcgccgag | 780 |
| gcctggggta | gagcagactg | tggctttacc | tcggtgtcct | accagcaagg | ggtcctgtct | 840 |
| gccaccatcc | tctatgagat | cctgctaggg | aaggccaccc | tgtatgctgt | gctggtcagc | 900 |
| gcccttgtgt | tgatggccat | ggtcaagaga | aaggatttct | ga | | 942 |

```
<210> SEQ ID NO 39
<211> LENGTH: 846
<212> TYPE: DNA
<213> ORGANISM: Homo sapiens

<400> SEQUENCE: 39
atggcatgcc ctggcttcct gtgggcactt gtgatctcca cctgtcttga atttagcatg      60
gctcagacag tcactcagtc tcaaccagag atgtctgtgc aggaggcaga gaccgtgacc     120
ctgagctgca catatgacac cagtgagagt gattattatt tattctggta caagcagcct     180
cccagcaggc agatgattct cgttattcgc caagaagctt ataagcaaca gaatgcaaca     240
gagaatcgtt tctctgtgaa cttccagaaa gcagccaaat ccttcagtct caagatctca     300
gactcacagc tggggatgc cgcgatgtat ttctgtgctt acacggttcc ctctaatgct      360
ggtggtacta gctatggaaa gctgacattt ggacaaggga ccatcttgac tgtccatcca     420
aatatccaga accctgaccc tgccgtgtac cagctgagag actctaaatc cagtgacaag     480
tctgtctgcc tattcaccga ttttgattct caaacaaatg tgtcacaaag taaggattct     540
gatgtgtata tcacagacaa aactgtgcta gacatgaggt ctatggactt caagagcaac     600
agtgctgtgg cctggagcaa caaatctgac tttgcatgtg caaacgcctt caacaacagc     660
attattccag aagacacctt cttccccagc ccagaaagtt cctgtgatgt caagctggtc     720
gagaaaagct ttgaaacaga tacgaaccta aactttcaaa acctgtcagt gattgggttc     780
cgaatcctcc tcctgaaagt ggccgggttt aatctgctca tgacgctgcg gctgtggtcc     840
agctga                                                               846

<210> SEQ ID NO 40
<211> LENGTH: 933
<212> TYPE: DNA
<213> ORGANISM: Homo sapiens

<400> SEQUENCE: 40
atggatacct ggctcgtatg ctgggcaatt tttagtctct tgaaagcagg actcacagaa      60
cctgaagtca cccagactcc cagccatcag gtcacacaga tgggacagga agtgatcttg     120
cgctgtgtcc ccatctctaa tcacttatac ttctattggt acagacaaat cttggggcag     180
aaagtcgagt ttctggtttc cttttataat aatgaaatct cagagaagtc tgaaatattc     240
gatgatcaat tctcagttga aaggcctgat ggatcaaatt tcactctgaa gatccggtcc     300
acaaagctgg aggactcagc catgtacttc tgtgccagca gtgaaagggg acagggttat     360
ggctacacct tcggttcggg gaccaggtta accgttgtag aggacctgaa caaggtgttc     420 ccaccccgagg tcgctgtgtt tgagccatca gaagcagaga tctcccacac ccaaaaggcc     480
acactggtgt gcctggccac aggcttcttc cccgaccacg tggagctgag ctggtgggtg     540
aatgggaagg aggtgcacag tggggtcagc acagacccgc agcccctcaa ggagcagccc     600
gccctcaatg actccagata ctgcctgagc agccgcctga gggtctcggc caccttctgg     660
cagaaccccc gcaaccactt ccgctgtcaa gtccagttct acgggctctc ggagaatgac     720
gagtggaccc aggataggc caaacccgtc acccagatcg tcagcgccga ggcctgggt      780 agagcagact gtggctttac ctcggtgtcc taccagcaag gggtcctgtc tgccaccatc     840
ctctatgaga tcctgctagg gaaggccacc ctgtatgctg tgctggtcag cgcccttgtg     900
ttgatggcca tggtcaagag aaaggatttc tga                                 933
```

```
<210> SEQ ID NO 41
<211> LENGTH: 816
<212> TYPE: DNA
<213> ORGANISM: Artificial Sequence
<220> FEATURE:
<223> OTHER INFORMATION: Synthetic

<400> SEQUENCE: 41
atggcatgcc ctggcttcct gtgggcactt gtgatctcca cctgtcttga atttagcatg      60
gctcagacag tcactcagtc tcaaccagag atgtctgtgc aggaggcaga gaccgtgacc     120
ctgagctgca catatgacac cagtgagagt gattattatt tattctggta caagcagcct     180
cccagcaggc agatgattct cgttattcgc caagaagctt ataagcaaca gaatgcaaca     240
gagaatcgtt tctctgtgaa cttccagaaa gcagccaaat ccttcagtct caagatctca     300
gactcacagc tgggggatgc cgcgatgtat ttctgtgctc tccggagctc aggaacctac     360
aaatacatct ttggaacagg caccaggctg aaggttttag caaatatcca gaaccctgaa     420
cctgctgtgt accagttaaa agatcctcgg tctcaggaca gcaccctctg cctgttcacc     480
gactttgact cccaaatcaa tgtgccgaaa accatggaat ctggaacgtt catcactgac     540
aaaactgtgc tggacatgaa agctatggat tccaagagca atggggccat tgcctggagc     600
aaccagacaa gcttcacctg ccaagatatc ttcaaagaga ccaacgccac ctaccccagt     660
tcagacgttc cctgtgatgc cacgttgact gagaaaagct ttgaaacaga tatgaaccta     720
aactttcaaa acctgtcagt tatgggactc cgaatcctcc tgctgaaagt agccggattt     780
aacctgctca tgacgctgag gctgtggtcc agttga                              816

<210> SEQ ID NO 42
<211> LENGTH: 930
<212> TYPE: DNA
<213> ORGANISM: Artificial Sequence
<220> FEATURE:
<223> OTHER INFORMATION: Synthetic

<400> SEQUENCE: 42
atgggcacca ggctcctctt ctgggtggcc ttctgtctcc tggggcaga tcacacagga       60 gctggagtct cccagtcccc cagtaacaag gtcacagaga agggaaagga tgtagagctc     120
aggtgtgatc caatttcagg tcatactgcc ctttactggt accgacagag cctggggcag     180
ggcctggagt ttttaattta cttccaaggc aacagtgcac cagacaaatc agggctgccc     240
agtgatcgct tctctgcaga gaggactggg ggatccgtct ccactctgac gatccagcgc     300
acacagcagg aggactcggc cgtgtatctc tgtgccagca tccggacagg gccttttttc     360
tctggaaaca ccatatattt tggagaggga agttggctca ctgttgtaga ggaccctgaga    420 aacgtgaccc cacccaaggt ctccttgttt gagccatcaa aagcagagat tgcaaacaaa     480
caaaaggcta ccctcgtgtg cttggccagg ggcttcttcc ctgaccacgt ggagctgagc     540
tggtgggtga atggcaagga ggtccacagt ggggtcagca cggaccctca ggcctacaag     600
gagagcaatt atagctactg cctgagcagc cgcctgaggg tctctgctac cttctggcac     660
aatcctcgaa accacttccg ctgccaagtg cagttccatg gctttcaga ggaggacaag     720 tggccagagg gctcacccaa acctgtcaca cagaacatca gtgcagaggc tgggggccga     780
gcagactgtg gaatcacttc agcatcctat catcaggggg ttctgtctgc aaccatcctc     840
tatgagatcc tactggggaa ggccacccta tatgctgtgc tggtcagtgg cctggtgctg     900
atggctatgg tcaaaagaaa gaactcatga                                     930
```

<210> SEQ ID NO 43
<211> LENGTH: 828
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (346)..(348)
<223> OTHER INFORMATION: nnn at 346-348 is AGC, GCC, or any codon that encodes Ser, Ala, Leu, Ile, Val, or Met
<220> FEATURE:
<221> NAME/KEY: misc_feature
<222> LOCATION: (349)..(351)
<223> OTHER INFORMATION: nnn at 349-351 is TCA, GCC, or any codon that encodes Ser, Ala, Leu, Ile, Val, or Met
<220> FEATURE:
<221> NAME/KEY: misc_feature
<222> LOCATION: (352)..(354)
<223> OTHER INFORMATION: 352-354 is GGA, GCC, or any codon that encodes Gly, Ala, Leu, Ile, Val, or Met
<220> FEATURE:
<221> NAME/KEY: misc_feature
<222> LOCATION: (355)..(357)
<223> OTHER INFORMATION: nnn at misc feature: nnn at 355-357 is ACC, GCC, or any codon that encodes Thr, Ala, Leu, Ile, Val, or Met

<400> SEQUENCE: 43

```
atggcatgcc ctggcttcct gtgggcactt gtgatctcca cctgtcttga atttagcatg      60
gctcagacag tcactcagtc tcaaccagag atgtctgtgc aggaggcaga gaccgtgacc     120
ctgagctgca catatgacac cagtgagagt gattattatt tattctggta caagcagcct     180
cccagcaggc agatgattct cgttattcgc caagaagctt ataagcaaca gaatgcaaca     240
gagaatcgtt tctctgtgaa cttccagaaa gcagccaaat ccttcagtct caagatctca     300
gactcacagc tgggggatgc cgcgatgtat ttctgtgctc tccggnnnnn nnnnnnntac     360
aaatacatct ttggaacagg caccaggctg aaggttttag caaatatcca gaaccctgac     420
cctgccgtgt accagctgag agactctaaa tccagtgaca gtctgtctg cctattcacc      480
gattttgatt ctcaaacaaa tgtgtcacaa agtaaggatt ctgatgtgta tatcacagac     540
aaaactgtgc tagacatgag gtctatggac ttcaagagca cagtgctgt ggcctggagc      600
aacaaatctg actttgcatg tgcaaacgcc ttcaacaaca gcattattcc agaagacacc     660
ttcttcccca gcccagaaag ttcctgtgat gtcaagctgg tcgagaaaag ctttgaaaca     720
gatacgaacc taaactttca aaacctgtca gtgattgggt tccgaatcct cctcctgaaa     780
gtggccgggt ttaatctgct catgacgctg cggctgtggt ccagctga                 828
```

<210> SEQ ID NO 44
<211> LENGTH: 942
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (343)..(345)
<223> OTHER INFORMATION: NNN at 343-345 is CGG, GCC, or any codon that encodes Arg, Ala, Leu, Ile, Val, or Met
<220> FEATURE:
<221> NAME/KEY: misc_feature
<222> LOCATION: (346)..(348)
<223> OTHER INFORMATION: NNN at 346-348 is ACA, GCC, or any codon that encodes Thr, Ala, Leu, Ile, Val, or Met
<220> FEATURE:
<221> NAME/KEY: misc_feature
<222> LOCATION: (349)..(351)
<223> OTHER INFORMATION: NNN at 349-351 is GGG, GCC, or any codon that encodes Gly, Ala, Leu, Ile, Val, or Met
<220> FEATURE:
<221> NAME/KEY: misc_feature
<222> LOCATION: (352)..(354)
<223> OTHER INFORMATION: NNN at 352-354 is CCT, GCC, or any codon that
      encodes Pro, Ala, Leu, Ile, Val, or Met

<400> SEQUENCE: 44

```
atgggcacca ggctcctctt ctgggtggcc ttctgtctcc tgggggcaga tcacacagga      60
gctggagtct cccagtcccc cagtaacaag gtcacagaga agggaaagga tgtagagctc     120
aggtgtgatc caatttcagg tcatactgcc ctttactggt accgacagag cctggggcag     180
ggcctggagt ttttaattta cttccaaggc aacagtgcac cagacaaatc agggctgccc     240
agtgatcgct tctctgcaga gaggactggg ggatccgtct ccactctgac gatccagcgc     300
acacagcagg aggactcggc cgtgtatctc tgtgccagca tcnnnnnnnn nnnnttttc     360
tctggaaaca ccatatattt tggagaggga agttggctca ctgttgtaga ggacctgaac     420
aaggtgttcc cacccgaggt cgctgtgttt gagccatcag aagcagagat ctcccacacc     480
caaaaggcca cactggtgtg cctggccaca ggcttcttcc ctgaccacgt ggagctgagc     540
tggtgggtga atgggaagga ggtgcacagt ggggtcagca cggacccgca gcccctcaag     600
gagcagcccg ccctcaatga ctccagatac tgcctgagca gccgcctgag ggtctcggcc     660
accttctggc agaaccccg caaccacttc cgctgtcaag tccagttcta cgggctctcg     720
gagaatgacg agtggaccca ggatagggcc aaacccgtca cccagatcgt cagcgccgag     780
gcctggggta gagcagactg tggctttacc tcggtgtcct accagcaagg ggtcctgtct     840
gccaccatcc tctatgagat cctgctaggg aaggccaccc tgtatgctgt gctggtcagc     900
gcccttgtgt tgatggccat ggtcaagaga aaggatttct ga                       942
```

<210> SEQ ID NO 45
<211> LENGTH: 314
<212> TYPE: PRT
<213> ORGANISM: Homo sapiens

<400> SEQUENCE: 45

```
Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Lys Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Asp Ser Leu Gln Leu
145                 150                 155                 160
```

Val Phe Gly Ile Glu Leu Met Glu Val Asp Pro Ile Gly His Val Tyr
            165                 170                 175

Ile Phe Ala Thr Cys Leu Gly Leu Ser Tyr Asp Gly Leu Leu Gly Asp
        180                 185                 190

Asn Gln Ile Met Pro Lys Thr Gly Phe Leu Ile Ile Leu Ala Ile
        195                 200                 205

Ile Ala Lys Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Phe Gly
225                 230                 235                 240

Asp Pro Lys Lys Leu Leu Thr Gln Tyr Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Ile Glu Thr Ser Tyr Val Lys Val Leu His
        275                 280                 285

His Met Val Lys Ile Ser Gly Gly Pro Arg Ile Ser Tyr Pro Leu Leu
    290                 295                 300

His Glu Trp Ala Leu Arg Glu Gly Glu Glu
305                 310

<210> SEQ ID NO 46
<211> LENGTH: 16
<212> TYPE: PRT
<213> ORGANISM: Homo sapiens

<400> SEQUENCE: 46

Lys Lys Leu Leu Thr Gln Tyr Phe Val Gln Glu Asn Tyr Leu Glu Tyr
1               5                   10                  15

<210> SEQ ID NO 47
<211> LENGTH: 14
<212> TYPE: PRT
<213> ORGANISM: Artificial Sequence
<220> FEATURE:
<223> OTHER INFORMATION: Synthetic

<400> SEQUENCE: 47

Lys Lys Leu Leu Thr Gln His Phe Val Gln Glu Asn Tyr Leu
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic

<400> SEQUENCE: 48

Lys Lys Leu Leu Thr Gln His Phe Val Gln Glu Asn Tyr
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic

<400> SEQUENCE: 49

Lys Lys Leu Leu Thr Gln His Phe Val Gln Glu Asn
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic

<400> SEQUENCE: 50

Lys Lys Leu Leu Thr Gln His Phe Val Gln Glu
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Synthetic

<400> SEQUENCE: 51

Leu Leu Thr Gln His Phe Val Gln Glu Asn Tyr Leu Glu Tyr
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic

<400> SEQUENCE: 52

Leu Thr Gln His Phe Val Gln Glu Asn Tyr Leu Glu Tyr
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic

<400> SEQUENCE: 53

Thr Gln His Phe Val Gln Glu Asn Tyr Leu Glu Tyr
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic

<400> SEQUENCE: 54

Gln His Phe Val Gln Glu Asn Tyr Leu Glu Tyr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic

<400> SEQUENCE: 55

His Phe Val Gln Glu Asn Tyr Leu Glu Tyr
1               5                   10

```
<210> SEQ ID NO 56
<211> LENGTH: 11
<212> TYPE: PRT
<213> ORGANISM: Artificial Sequence
<220> FEATURE:
<223> OTHER INFORMATION: Synthetic

<400> SEQUENCE: 56

Gln Tyr Phe Val Gln Glu Asn Tyr Leu Glu Tyr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic

<400> SEQUENCE: 57

Gln Asp Leu Val Gln Glu Asn Tyr Leu Glu Tyr
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic

<400> SEQUENCE: 58

Gln Asp Trp Val Gln Glu Asn Tyr Leu Glu Tyr
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Synthetic

<400> SEQUENCE: 59

Gln Glu Trp Val Gln Glu Asn Tyr Leu Glu Tyr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Synthetic

<400> SEQUENCE: 60

Gln Asp Leu Val Gln Glu Lys Tyr Leu Glu Tyr
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic

<400> SEQUENCE: 61

Lys Asp Leu Val Gln Glu Lys Tyr Leu Glu Tyr
1               5                   10
```

```
<210> SEQ ID NO 62
<211> LENGTH: 11
<212> TYPE: PRT
<213> ORGANISM: Artificial Sequence
<220> FEATURE:
<223> OTHER INFORMATION: Synthetic

<400> SEQUENCE: 62

Lys Asp Leu Val Lys Glu Asn Tyr Leu Glu Tyr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic

<400> SEQUENCE: 63

Lys Asp Phe Val Lys Glu Lys Tyr Leu Glu Tyr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic

<400> SEQUENCE: 64

Lys Val Trp Val Gln Glu His Tyr Leu Glu Tyr
1               5                   10

<210> SEQ ID NO 65
<211> LENGTH: 16
<212> TYPE: PRT
<213> ORGANISM: Artificial Sequence
<220> FEATURE:
<223> OTHER INFORMATION: Synthetic

<400> SEQUENCE: 65

Arg Lys Leu Ile Thr Asp Asp Phe Val Lys Gln Lys Tyr Leu Glu Tyr
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Synthetic

<400> SEQUENCE: 66

Lys Lys Leu Ile Thr Asp Glu Phe Val Lys Gln Lys Tyr Leu Asp Tyr
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Synthetic

<400> SEQUENCE: 67

Lys Lys Leu Ile Thr Glu Val Phe Val Arg Gln Lys Tyr Leu Glu Tyr
1               5                   10                  15
```

```
<210> SEQ ID NO 68
<211> LENGTH: 16
<212> TYPE: PRT
<213> ORGANISM: Artificial Sequence
<220> FEATURE:
<223> OTHER INFORMATION: Synthetic

<400> SEQUENCE: 68

Lys Lys Leu Ile Thr Glu Asp Phe Val Arg Gln Arg Tyr Leu Glu Tyr
1               5                   10                  15

<210> SEQ ID NO 69
<211> LENGTH: 11
<212> TYPE: PRT
<213> ORGANISM: Artificial Sequence
<220> FEATURE:
<223> OTHER INFORMATION: Synthetic

<400> SEQUENCE: 69

Glu Glu Phe Val Gln Met Asn Tyr Leu Lys Tyr
1               5                   10

<210> SEQ ID NO 70
<211> LENGTH: 16
<212> TYPE: PRT
<213> ORGANISM: Artificial Sequence
<220> FEATURE:
<223> OTHER INFORMATION: Synthetic

<400> SEQUENCE: 70

Lys Lys Leu Leu Thr Gln Asp Leu Val Gln Glu Asn Tyr Leu Glu Tyr
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Synthetic

<400> SEQUENCE: 71

Lys Lys Leu Leu Thr Gln Asp Leu Val Gln Glu Lys Tyr Leu Glu Tyr
1               5                   10                  15
```

T CELL RECEPTORS RECOGNIZING MHC CLASS II-RESTRICTED MAGE-A3

CROSS-REFERENCE TO RELATED APPLICATIONS

This application is a U.S. National Phase of International Patent Application No. PCT/US2013/059608, filed Sep. 13, 2013, which claims the benefit of U.S. Provisional Application No. 61/701,056, filed on Sep. 14, 2012, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 63,935 Byte ASCII (Text) file named "719665ST25.TXT," dated Jan. 22, 2015.

BACKGROUND OF THE INVENTION

Adoptive cell therapy (ACT) involves the transfer of reactive T cells into patients, including the transfer of tumor-reactive T cells into cancer patients. Adoptive cell therapy using T-cells that target human leukocyte antigen (HLA)-A*02 restricted T-cell epitopes has been successful in causing the regression of tumors in some patients. However, patients that lack HLA-A*02 expression cannot be treated with T-cells that target HLA-A*02 restricted T-cell epitopes. Such a limitation creates an obstacle to the widespread application of adoptive cell therapy. Accordingly, there exists a need for improved immunological compositions and methods for treating cancer.

BRIEF SUMMARY OF THE INVENTION

An embodiment of the invention provides an isolated or purified T-cell receptor (TCR), and functional portions and functional variants thereof, having antigenic specificity for MAGE-A3$_{243-258}$ and MAGE-A6.

Another embodiment of the invention provides an isolated or purified TCR comprising (a) SEQ ID NOs: 3-8 or (b) SEQ ID NOs: 21-22, or a functional variant of (a) or (b), wherein the functional variant comprises (a) or (b) with at least one amino acid substitution in any one or more of (a) or any one or more of (b), and the functional variant has antigenic specificity for MAGE-A3 in the context of HLA-DPβ1*04.

The invention further provides related polypeptides and proteins, as well as related nucleic acids, recombinant expression vectors, host cells, and populations of cells. Further provided by the invention are antibodies, or antigen binding portions thereof, and pharmaceutical compositions relating to the TCRs (including functional portions and functional variants thereof) of the invention.

Methods of detecting the presence of cancer in a mammal and methods of treating or preventing cancer in a mammal are further provided by the invention. The inventive method of detecting the presence of cancer in a mammal comprises (i) contacting a sample comprising cells of the cancer with any of the inventive TCRs (including functional portions and functional variants thereof), polypeptides, proteins, nucleic acids, recombinant expression vectors, host cells, populations of host cells, or antibodies, or antigen binding portions thereof, described herein, thereby forming a complex, and (ii) detecting the complex, wherein detection of the complex is indicative of the presence of cancer in the mammal.

The inventive method of treating or preventing cancer in a mammal comprises administering to the mammal any of the TCRs (including functional portions and functional variants thereof), polypeptides, or proteins described herein, any nucleic acid or recombinant expression vector comprising a nucleotide sequence encoding any of the TCRs (including functional portions and functional variants thereof), polypeptides, proteins described herein, or any host cell or population of host cells comprising a recombinant vector which encodes any of the TCRs (including functional portions and functional variants thereof), polypeptides, or proteins described herein, in an amount effective to treat or prevent cancer in the mammal.

BRIEF DESCRIPTION OF THE SEVERAL VIEWS OF THE DRAWING(S)

FIGS. 1A and 1B are bar graphs showing interferon (IFN)-gamma secretion (pg/ml) by CD4+ T cells from first (1A) and second (1B) donors in response to co-culture with 293-CIITA target cells untransfected (292-CIITA) or transfected with full length NY-ESO-1 (293-CIITA-NY-ESO-1) protein, MAGE-A1 protein (293-CIITA-MAGE A1), MAGE-A3 protein (293-CIITA-MAGE-A3), MAGE-A6 protein (293-CIITA-MAGE-A6), or MAGE A12 protein (293-CIITA-MAGE-A12). The T cells were untransduced (UT) or transduced with F5 (anti-MART-1) TCR, R12C9 TCR, or 6F9 TCR.

Figure 5:
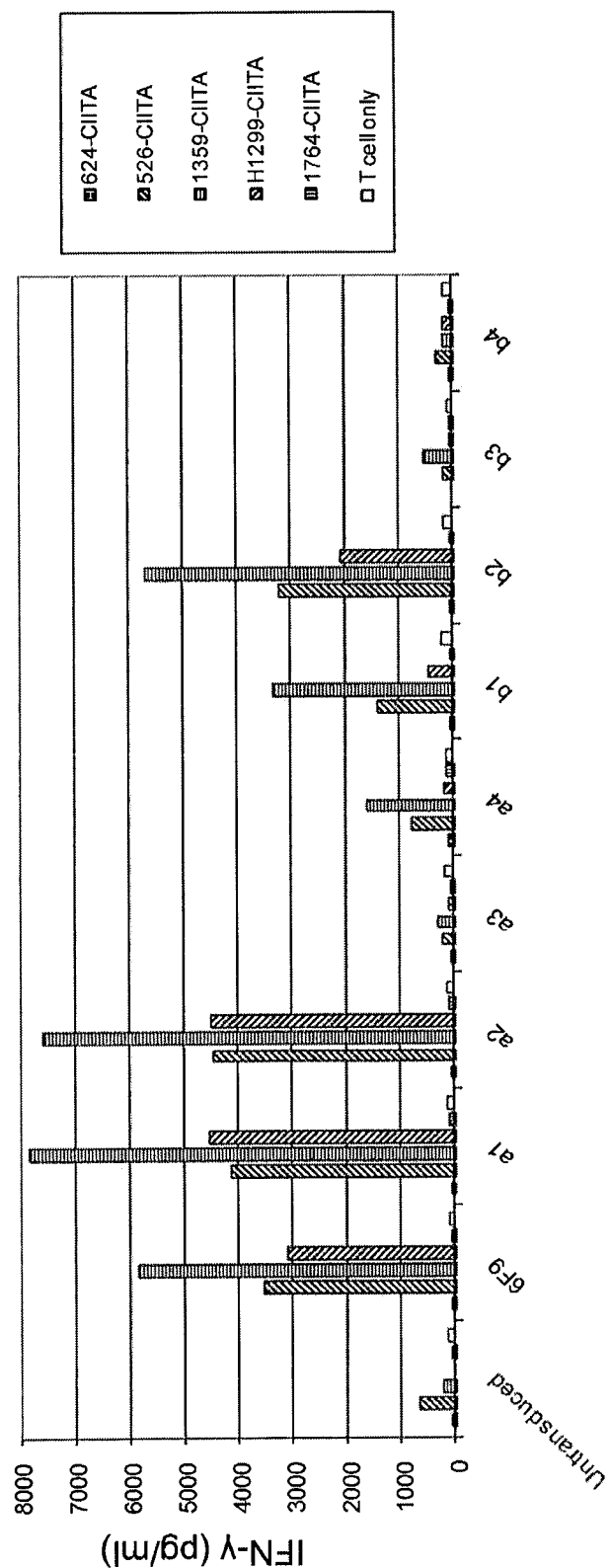

FIG. 5 is a bar graph showing IFN-gamma (pg/ml) secretion by PBL that were untransduced or transduced with wild-type (wt) 6F9 TCR or one of each of eight substituted TCRs: a1 (alpha chain S116A), a2 (alpha chain S117A), a3 (alpha chain G118A), a4 (alpha chain T119A), b1 (beta chain R115A), b2 (beta chain T116A), b3 (beta chain GJ 17A), or b4 (beta chain P118A) upon culture alone (T cell only; unshaded bars) or co-culture with 624-CIITA (checkered bars), 526-CIITA (right crosshatched bars), 1359-CIITA (horizontal striped bars), H1299-CIITA (left crosshatched bars), or 1764-CIITA (vertical striped bars).

Figure 6:
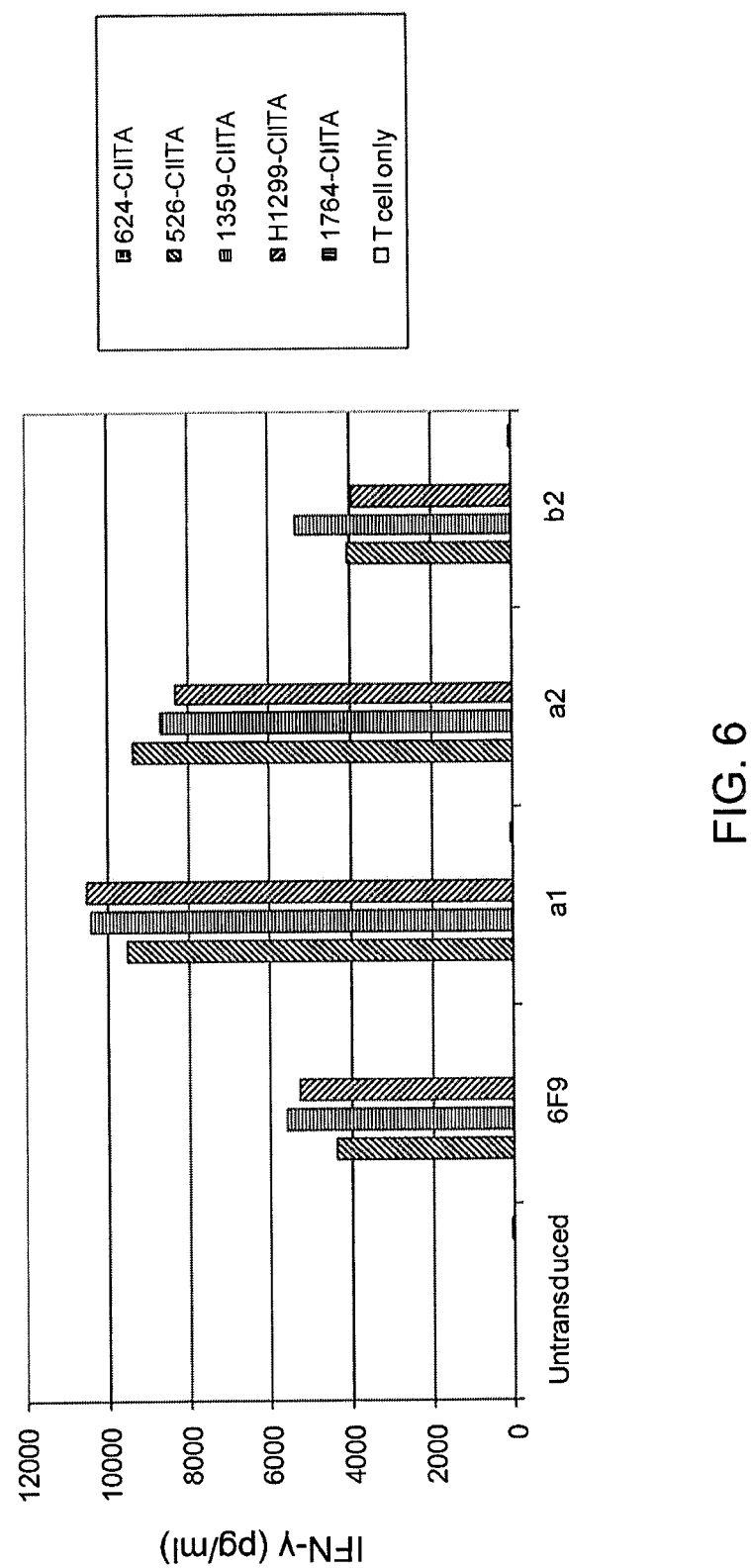

FIG. 6 is a bar graph showing IFN-gamma (pg/ml) secretion by CD4+ enriched PBL that were untransduced or transduced with wild-type (wt) 6F9 TCR or one of each of three substituted TCRs: a1 (alpha chain S116A), a2 (alpha chain S117A), or b2 (beta chain T116A) upon culture alone (T cell only; unshaded bars) or co-culture with 624-CIITA (checkered bars), 526-CIITA (right crosshatched bars), 1359-CIITA (horizontal striped bars), H1299-CIITA (left crosshatched bars), or 1764-CIITA (vertical striped bars).

Figure 7:
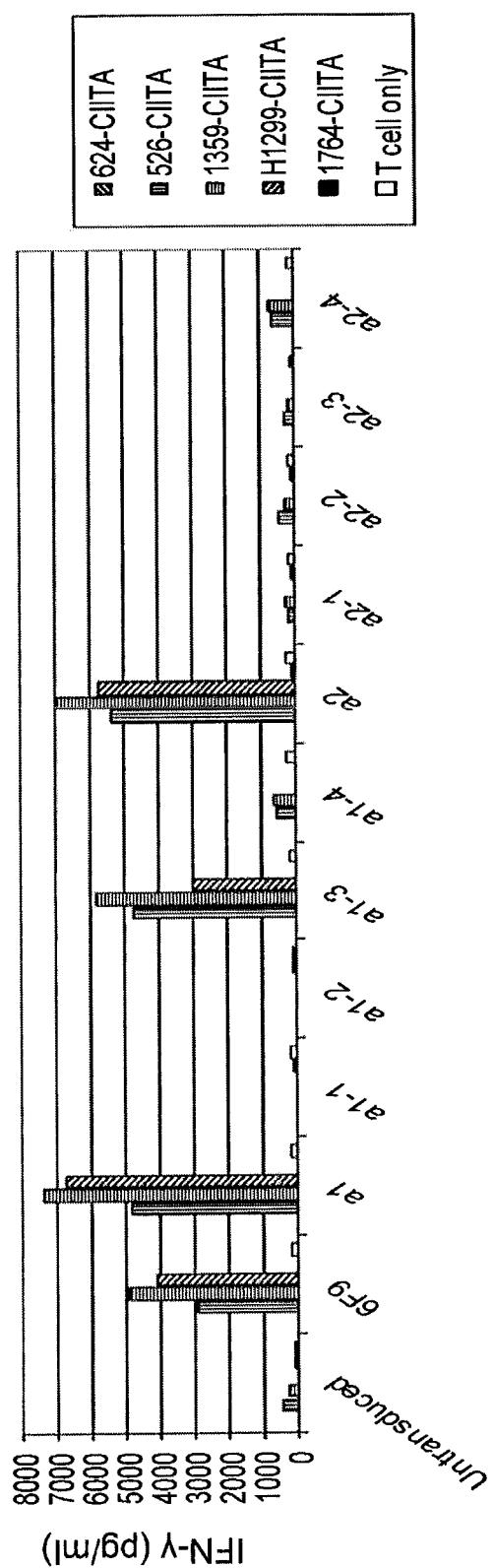

FIG. 7 is a bar graph showing IFN-gamma (pg/ml) secretion by PBL that were untransduced or transduced with wild-type (wt) 6F9 TCR or one of each of ten substituted TCRs: a1 (alpha chain S116A), a2 (alpha chain S117A), a1-1 (alpha chain S116L), a1-2 (alpha chain S116I), a1-3 (alpha chain S116V), a1-4 (alpha chain S116M), a2-1 (alpha chain S117L), a2-2 (alpha chain S117I), a2-3 (alpha chain S117V), or a2-4 (alpha chain S117M) upon culture alone or (T cell only; unshaded bars) or co-culture with 624-CIITA (right crosshatched bars), 526-CIITA (vertical striped bars), 1359-CIITA (horizontal striped bars), H1299-CIITA (left crosshatched bars), or 1764-CIITA (black bars).

Figure 8:
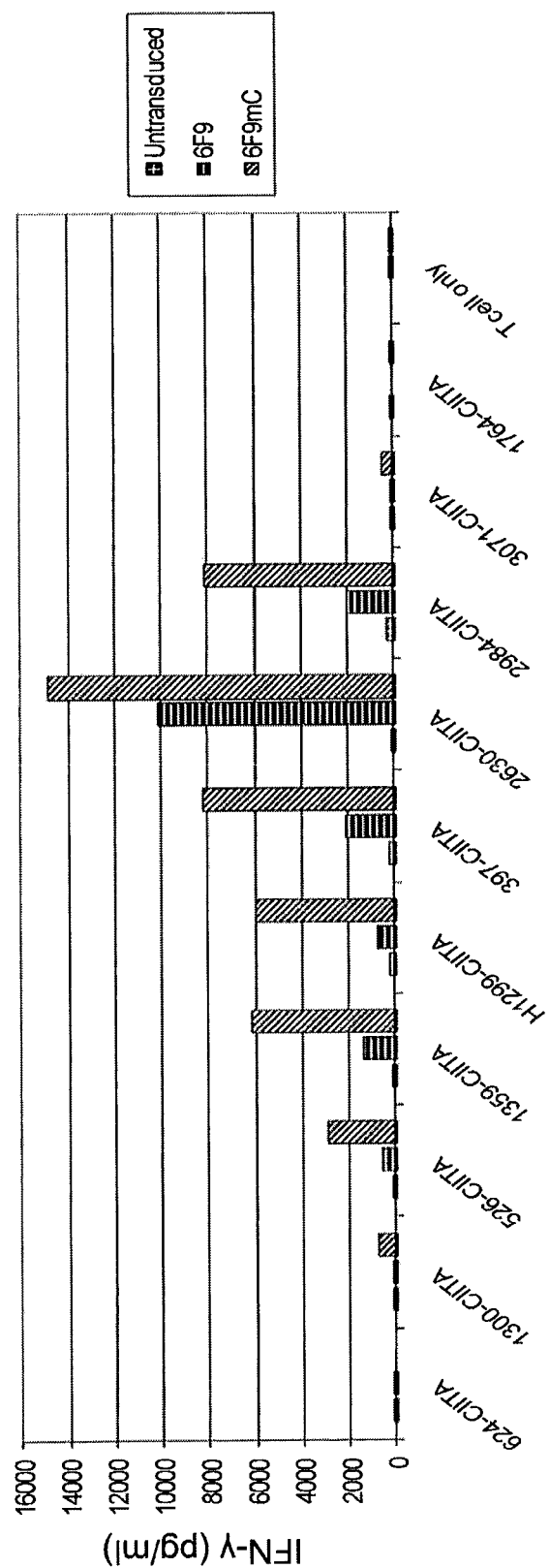

FIG. 8 is a bar graph showing IFN-gamma (pg/ml) secretion by PBL that were untransduced (checkered bars) or transduced with wild-type (wt) 6F9 TCR (horizontal striped bar) or 6F9mC TCR (SEQ ID NOs: 27 and 28) (left crosshatched bars) upon culture alone (T cells only) or co-culture with 624-CIITA, 1300-CIITA, 526-CIITA, 1359-CIITA, H1299-CIITA, 397-CIITA, 2630-CIITA, 2984-CIITA, 3071-CIITA, or 1764-CIITA cells.

Figure 9:
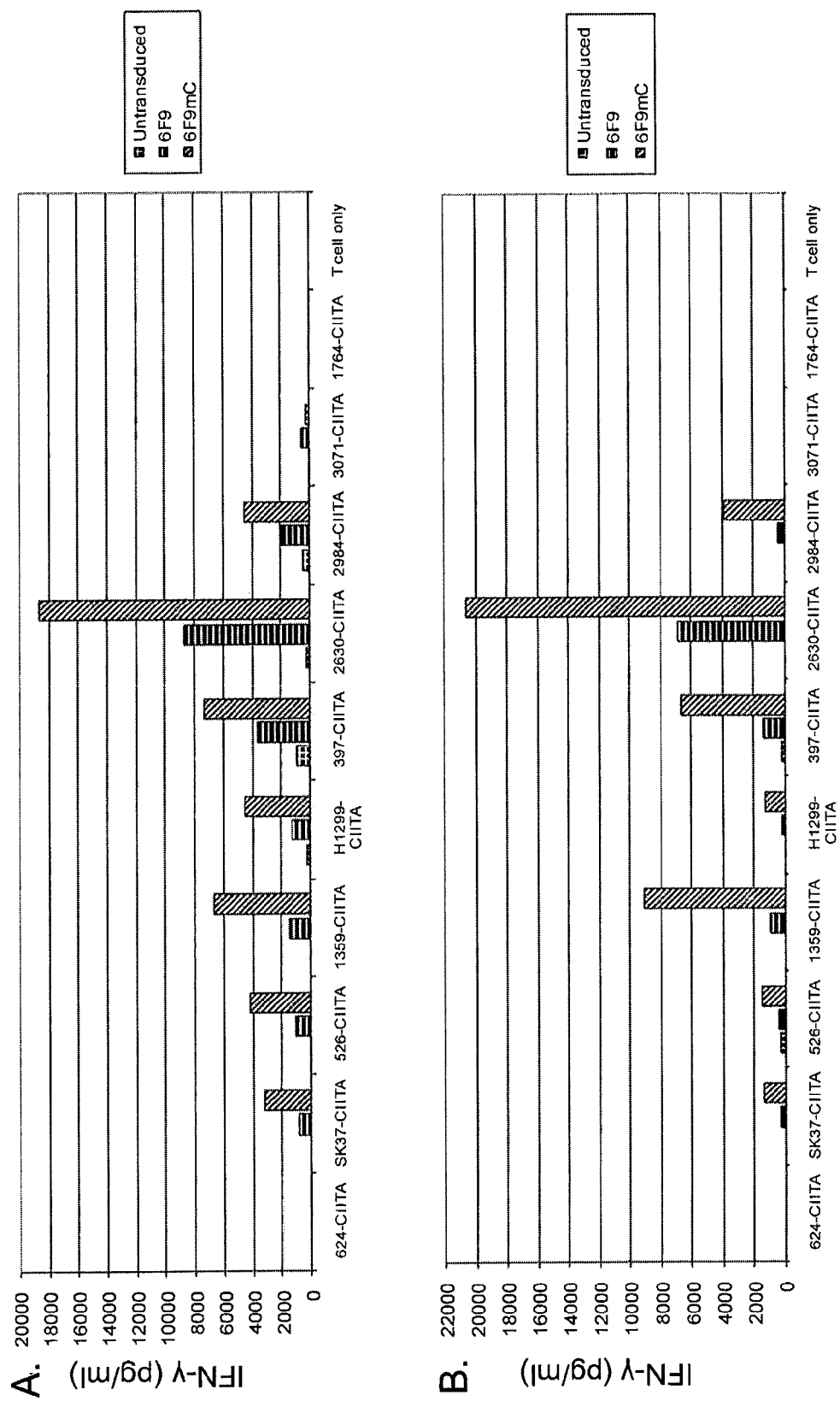

FIGS. 9A and 9B are bar graphs showing IFN-gamma (pg/ml) secretion by CD4+ (9A) or CD8+ (9B) enriched PBL that were untransduced (checkered bars) or transduced with wild-type (wt) 6F9 TCR (horizontal striped bar) or 6F9mC TCR (SEQ ID NOs: 27 and 28) (left crosshatched bars) upon culture alone (T cells only) or co-culture with 624-CIITA, SK37-CIITA, 526-CIITA, 1359-CIITA, H1299-CIITA, 397-CIITA, 2630-CIITA, 2984-CIITA, 3071-CIITA, or 1764-CIITA cells.

Figure 10:
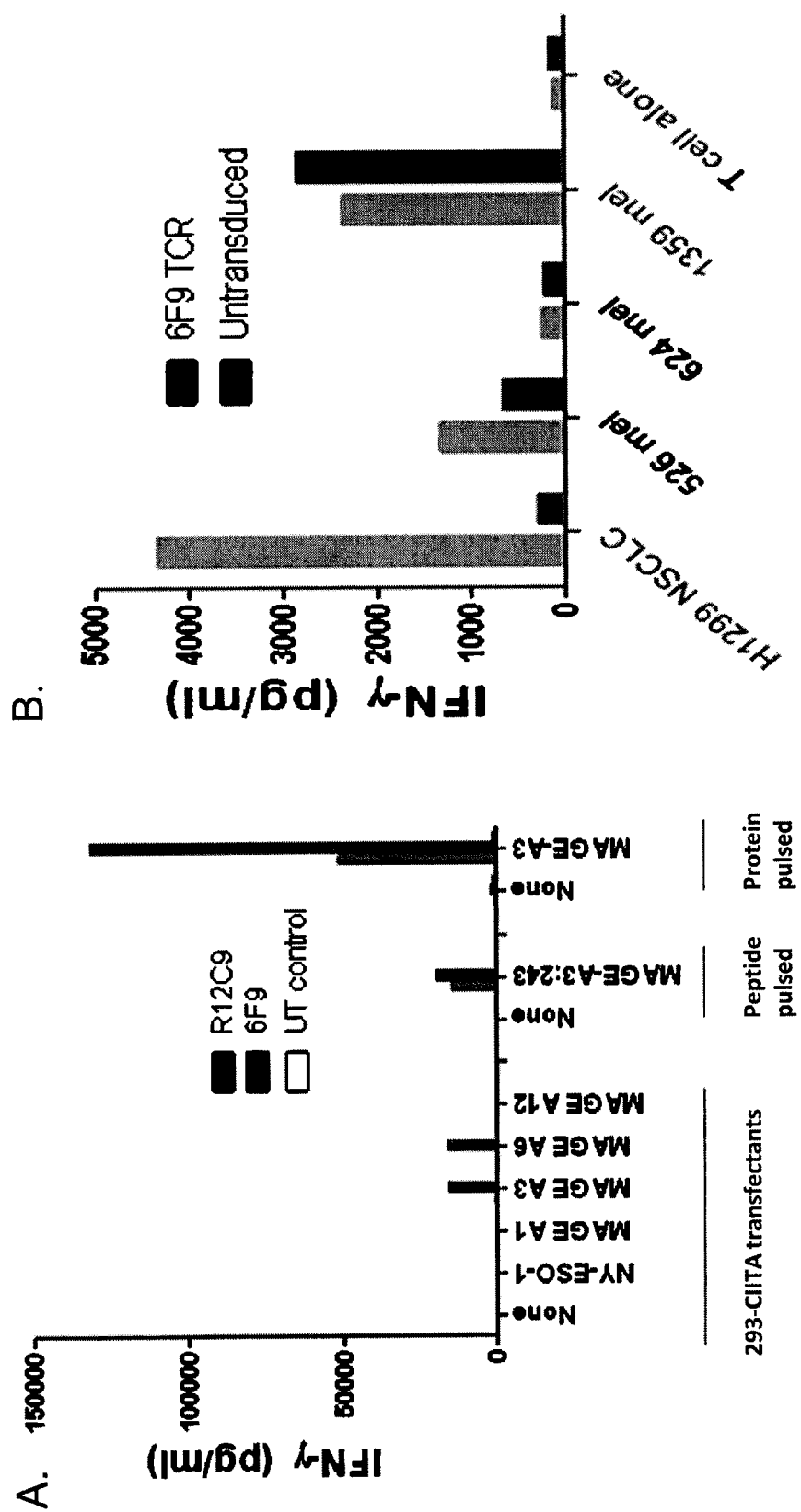

FIG. 10A is a bar graph showing IFN-gamma secretion by PBL that were untransduced (UT; unshaded bars) or transduced with R12C9 TCR (grey bars) or 6F9 TCR (black bars) upon culture alone (none) or co-culture with 293-CIITA transfectants that were transfected with full length NY-ESO-1 protein, MAGE-A1 protein, MAGE-A3 protein, MAGE-A6 protein, MAGE-A12 protein, or 293-CIITA cells that were pulsed with MAGE-A3$_{243-258}$ peptide or MAGE-A3 protein.

FIG. 10B is a bar graph showing IFN-gamma secretion by PBL that were untransduced (UT; black bars) or transduced with 6F9 TCR (grey bars) upon culture alone (T cell alone) or co-culture with non-small cell lung cancer (NSCLC) cell line H11299 or melanoma cell line 526 mel, 624 mel, or 1359 mel.

DETAILED DESCRIPTION OF THE INVENTION

The invention provides an isolated or purified T cell receptor (TCR), and functional portions and functional variants thereof, having antigenic specificity for MAGE-A3, wherein the TCR recognizes MAGE-A3 in the context of HLA-DPβ1*04. In an embodiment of the invention, the isolated or purified TCR has antigenic specificity for MAGE-A3$_{243-258}$ and MAGE-A6.

MAGE-A3 and MAGE-A6 are members of the MAGE-A family of twelve homologous proteins, also including MAGE-A1, MAGE-A2, MAGE-A4, MAGE-A5, MAGE-A7, MAGE-A8, MAGE-A9, MAGE-A10, MAGE-A11, and MAGE-A12. The MAGE-A proteins are cancer testis antigens (CTA), which are expressed only in tumor cells and non-MHC expressing germ cells of the testis and placenta. MAGE-A proteins are expressed in a variety of human cancers including, but not limited to, melanoma, breast cancer, leukemia, thyroid cancer, gastric cancer, pancreatic cancer, liver cancer (e.g., hepatocellular carcinoma), lung cancer (e.g., non-small cell lung carcinoma), ovarian cancer, multiple myeloma, esophageal cancer, kidney cancer, head cancers (e.g., squamous cell carcinoma), neck cancers (e.g., squamous cell carcinoma), prostate cancer, synovial cell sarcoma, and urothelial cancer.

The TCRs (including functional portions and functional variants thereof) of the invention provide many advantages, including when used for adoptive cell transfer. For example, by targeting MAGE-A3 that is presented in the context of HLA-DPβ1*04, the inventive TCRs (including functional portions and functional variants thereof) make it possible to treat patients who are unable to be treated using TCRs that target MAGE antigens that are presented in the context of other HLA molecules, e.g., HLA-A*02, HLA-A*01, or HLA-C*07. HLA-DPβ1*04 is a highly prevalent allele that is expressed by from about 70% to about 80% of the cancer patient population. Accordingly, the inventive TCRs (including functional portions and functional variants thereof) advantageously greatly expand the patient population that can be treated. Additionally, without being bound by a particular theory, it is believed that because MAGE-A3 and/or MAGE-A6 are expressed by cells of multiple cancer types, the inventive TCRs (including functional portions and functional variants thereof) advantageously provide the ability to destroy cells of multiple types of cancer and, accordingly, treat or prevent multiple types of cancer. Additionally, without being bound to a particular theory, it is believed that because the MAGE-A proteins are cancer testis antigens that are expressed only in tumor cells and non-MHC expressing germ cells of the testis and placenta, the inventive TCRs (including functional portions and functional variants thereof) advantageously target the destruction of cancer cells while minimizing or eliminating the destruction of normal, non-cancerous cells, thereby reducing, for example, by minimizing or eliminating, toxicity.

The phrase "antigenic specificity" as used herein means that the TCR can specifically bind to and immunologically recognize MAGE-A3 and/or MAGE-A6 with high avidity. For example, a TCR may be considered to have "antigenic specificity" for MAGE-A3 and/or MAGE-A6 if T cells expressing the TCR secrete at least about 200 pg/ml or more (e.g., 200 pg/ml or more, 300 pg/ml or more, 400 pg/ml or more, 500 pg/ml or more, 600 pg/ml or more, 700 pg/ml or more, 1000 pg/ml or more, 5,000 pg/ml or more, 7,000 pg/ml or more, 10,000 pg/ml or more, or 20,000 pg/ml or more) of IFN-γ upon co-culture with antigen-negative HLA-DPβ1*04+ target cells pulsed with a low concentration of MAGE-A3 and/or MAGE-A6 peptide (e.g., about 0.05 ng/ml to about 5 ng/ml, 0.05 ng/ml, 0.1 ng/ml, 0.5 ng/ml, 1 ng/ml, or 5 ng/ml). Alternatively or additionally, a TCR may be considered to have "antigenic specificity" for MAGE-A3 and/or MAGE-A6 if T cells expressing the TCR secrete at least twice as much IFN-γ as the untransduced PBL background level of IFN-γ upon co-culture with antigen-negative HLA-DPβ1*04+ target cells pulsed with a low concentration of MAGE-A3 and/or MAGE-A6 peptide. The inventive TCRs (including functional portions and functional variants thereof) may also secrete IFN-γ upon co-culture with antigen-negative HLA-DPβ1*04+ target cells pulsed with higher concentrations of MAGE-A3 and/or MAGE-A6 peptide.

An embodiment of the invention provides a TCR (including functional portions and variants thereof) with antigenic specificity for any MAGE-A3 protein, polypeptide or peptide. The inventive TCR (including functional portions and functional variants thereof) may have antigenic specificity for a MAGE-A3 protein comprising, consisting of, or consisting essentially of, SEQ ID NO: 1. In a preferred embodiment of the invention, the TCR (including functional portions and variants thereof) has antigenic specificity for a MAGE-A3$_{243-258}$ peptide comprising, consisting of, or consisting essentially of, KKLLTQHFVQENYLEY (SEQ ID NO: 2).

The inventive TCRs (including functional portions and functional variants thereof) are able to recognize MAGE-A3 in a human leukocyte antigen (HLA)-DPβ1*04-dependent manner. "HLA-DPβ1*04-dependent manner," as used herein, means that the TCR elicits an immune response upon binding to a MAGE-A3 protein, polypeptide or peptide within the context of an HLA-DPβ1*04 molecule. The inventive TCRs (including functional portions and functional variants thereof) are able to recognize MAGE-A3 that is presented by an HLA-DPβ1*04 molecule and may bind to the HLA-DPβ1*04 molecule in addition to MAGE-A3. Exemplary HLA-DPβ1*04 molecules, in the context of which the inventive TCRs (including functional portions and functional variants thereof) recognize MAGE-A3, include those encoded by the HLA-DPβ1*0401 and/or HLA-DPβ1*0402 alleles.

An embodiment of the invention provides a TCR (including functional portions and variants thereof) with antigenic specificity for any MAGE-A6 protein, polypeptide or peptide. The inventive TCR (including functional portions and functional variants thereof) may have antigenic specificity for a MAGE-A6 protein comprising, consisting of, or consisting essentially of, SEQ ID NO: 45. In a preferred embodiment of the invention, the TCR (including functional portions and functional variants thereof) has antigenic specificity for a MAGE-A6$_{243-258}$ peptide comprising, consisting of, or consisting essentially of, KKLLTQYFVQENYLEY (SEQ ID NO: 46).

The invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for MAGE-A3 in the context of HLA-DPβ1*04.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 3 or 13 (CDR1 of α chain), a CDR2 comprising the amino acid sequence of SEQ ID NO: 4 or 14 (CDR2 of α chain), and a CDR3 comprising the amino acid sequence of SEQ ID NO: 5 or 15 (CDR3 of α chain), and a second polypeptide chain comprising a CDR1 comprising the amino acid sequence of SEQ ID NO: 6 or 16 (CDR1 of β chain), a CDR2 comprising the amino acid sequence of SEQ ID NO: 7 or 17 (CDR2 of β chain), and a CDR3 comprising the amino acid sequence of SEQ ID NO: 8 or 18 (CDR3 of β chain). In this regard, the inventive TCR can comprise any one or more of the amino acid sequences selected from the group consisting of any one or more of SEQ ID NOs: 3-5, 6-8, 13-15, and 16-18. Preferably the TCR comprises the amino acid sequences of SEQ ID NOs: 3-8 or 13-18. More preferably the TCR comprises the amino acid sequences of SEQ ID NOs: 3-8.

Alternatively or additionally, the TCR can comprise an amino acid sequence of a variable region of a TCR comprising the CDRs set forth above. In this regard, the TCR can comprise the amino acid sequence of SEQ ID NO: 9 or 19 (the variable region of an α chain) or 10 or 20 (the variable region of a β chain), both SEQ ID NOs: 9 and 10 or both SEQ ID NOs: 19 and 20. Preferably, the inventive TCR comprises the amino acid sequences of both SEQ ID NOs: 9 and 10.

Alternatively or additionally, the TCR can comprise an α chain of a TCR and a β chain of a TCR. Each of the α chain and β chain of the inventive TCR can independently comprise any amino acid sequence. Preferably, the α chain comprises the variable region of an α chain as set forth above. In this regard, the inventive TCR can comprise the amino acid sequence of SEQ ID NO: 11 or 21. An α chain of this type can be paired with any β chain of a TCR. Preferably, the β chain of the inventive TCR comprises the variable region of a β chain as set forth above. In this regard, the inventive TCR can comprise the amino acid sequence of SEQ ID NO: 12 or 22. The inventive TCR, therefore, can comprise the amino acid sequence of SEQ ID NO: 11, 12, 21, or 22, both SEQ ID NOs: 11 and 12 or both SEQ ID NOs: 21 and 22. Preferably, the inventive TCR comprises the amino acid sequences of both SEQ ID NOs: 11 and 12.

Included in the scope of the invention are functional variants of the inventive TCRs described herein. The term "functional variant" as used herein refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to MAGE-A3 and/or MAGE-A6 for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

In this regard, an embodiment of the invention provides an isolated or purified TCR comprising (a) SEQ ID NOs: 3-8, (b) SEQ ID NOs: 21-22, or a functional variant of (a) or (b), wherein the functional variant comprises (a) or (b) with at least one amino acid substitution in any one or more of (a) or any one or more of (b), and the functional variant has antigenic specificity for MAGE-A3 in the context of HLA-DPβ1*04. Preferably, the amino acid substitution is located in a CDR3 region of the alpha or beta chain, preferably in the CDR3 region of the alpha chain. In some embodiments, the functional variant (or functional portions thereof) provide an increased reactivity against MAGE-A3 as compared to the parent TCR amino acid sequence. In general, the substituted α chain amino acid sequences SEQ ID NOs: 29, 31, and 33 correspond with all or portions of the native, unsubstituted SEQ ID NO: 11 (TCR α chain), with SEQ ID NOs: 29, 31, and 33 having at least one substitution when compared to SEQ ID NO: 11. Preferably, one or more of the native Ser116, Ser117, Gly118, and Thr119 is substituted. Likewise, the substituted β chain amino acid sequences SEQ ID NOs: 30, 32, and 34 correspond with all or portions of the native, unsubstituted SEQ ID NO: 12 (TCR β chain), with SEQ ID NOs: 30, 32, and 34 having at least one substitution when compared to SEQ ID NO: 12. Preferably, one or more of the native Arg115, Thr116, Gly117, and Pro118 is substituted.

In particular, the invention provides a functional variant of a TCR comprising (i) SEQ ID NO: 29, wherein Xaa4 is Ser, Ala, Leu, Ile, Val, or Met; Xaa5 is Ser, Ala, Leu, Ile, Val, or Met; Xaa6 is Gly, Ala, Leu, Ile, Val, or Met; and Xaa7 is Thr, Ala, Leu, Ile, Val, or Met and/or (ii) SEQ ID NO: 30, wherein Xaa4 is Arg, Ala, Leu, Ile, Val, or Met; Xaa5 is Thr, Ala, Leu, Ile, Val, or Met; Xaa6 is Gly, Ala, Leu, Ile, Val, or Met; and Xaa7 is Pro, Ala, Leu, Ile, Val, or Met. SEQ ID NO: 29 generally corresponds to positions 113-123 of the native, unsubstituted SEQ ID NO: 11 with the exception that in SEQ ID NO: 29, one or more of Ser4, Ser5, Gly6, and Thr7 is substituted. Preferably, the functional variant comprises (a) SEQ ID NO: 29, wherein Xaa4 is Ala, Xaa5 is Ser, Xaa6 is Gly, and Xaa7 is Thr, or (b) SEQ ID NO: 29, wherein Xaa4 is Ser, Xaa5 is Ala, Xaa6 is Gly, and Xaa7 is Thr. Although in some embodiments, SEQ ID NO: 29 may comprise wild-type CDR3α SEQ ID NO: 5, preferably, SEQ ID NO: 29 does not comprise SEQ ID NO: 5. SEQ ID NO: 30 generally corresponds to positions 112-126 of the native, unsubstituted SEQ ID NO: 12 with the exception that in SEQ ID NO: 30, one or more of Arg4, Thr5, Gly6, and Pro7 is substituted. Although in some embodiments, SEQ ID NO: 30 may comprise wild-type CDR3β SEQ ID NO: 8, preferably, SEQ ID NO: 30 does not comprise SEQ ID NO: 8.

The invention also provides a functional variant of a TCR comprising (i) SEQ ID NO: 31, wherein Xaa116 is Ser, Ala, Leu, Ile, Val, or Met; Xaa117 is Ser, Ala, Leu, Ile, Val, or Met; Xaa118 is Gly, Ala, Leu, Ile, Val, or Met; and Xaa119 is Thr, Ala, Leu, Ile, Val, or Met; and/or (ii) SEQ ID NO: 32, wherein Xaa115 is Arg, Ala, Leu, Ile, Val, or Met; Xaa116 is Thr, Ala, Leu, Ile, Val, or Met; Xaa117 is Gly, Ala, Leu, Ile, Val, or Met; and Xaa118 is Pro, Ala, Leu, Ile, Val, or Met. SEQ ID NO: 31 generally corresponds to positions 1-134 of the native, unsubstituted SEQ ID NO: 11 with the exception that in SEQ ID NO: 31, one or more of one or more of Ser116, Ser117, Gly118, and Thr119 is substituted. Preferably, the functional variant comprises (a) SEQ ID NO: 31, wherein Xaa116 is Ala, Xaa117 is Ser, Xaa118 is Gly, and Xaa119 is Thr, or (b) SEQ ID NO: 31, wherein Xaa116 is Ser, Xaa117 is Ala, Xaa118 is Gly, and Xaa119 is Thr. Although in some embodiments, SEQ ID NO: 31 may comprise wild-type CDR3α SEQ ID NO: 5, preferably, SEQ ID NO: 31 does not comprise SEQ ID NO: 5. SEQ ID NO: 32 generally corresponds to positions 1-137 of the native, unsubstituted SEQ ID NO: 12 with the exception that in SEQ ID NO: 32, one or more of one or more of Arg115, Thr116, Gly117, and Pro118 is substituted. Although in some embodiments, SEQ ID NO: 32 may comprise wild-type CDR3β SEQ ID NO: 8, preferably, SEQ ID NO: 32 does not comprise SEQ ID NO: 8.

Also provided by the invention is functional variant of a TCR comprising (i) SEQ ID NO: 33, wherein Xaa116 is Ser, Ala, Leu, Ile, Val, or Met; Xaa117 is Ser, Ala, Leu, Ile, Val, or Met; Xaa118 is Gly, Ala, Leu, Ile, Val, or Met; and Xaa119 is Thr, Ala, Leu, Ile, Val, or Met; and/or (ii) SEQ ID NO: 34, wherein Xaa115 is Arg, Ala, Leu, Ile, Val, or Met; Xaa116 is Thr, Ala, Leu, Ile, Val, or Met; Xaa117 is Gly, Ala, Leu, Ile, Val, or Met; and Xaa118 is Pro, Ala, Leu, Ile, Val, or Met. SEQ ID NO: 33 generally corresponds to positions 1-275 of the native, unsubstituted SEQ ID NO: 11 with the exception that in SEQ ID NO: 33, one or more of one or more of Ser116, Ser117, Gly118, and Thr119 is substituted. Preferably, the functional variant comprises (a) SEQ ID NO: 33, wherein Xaa116 is Ala, Xaa117 is Ser, Xaa118 is Gly, and Xaa119 is Thr, or (b) SEQ ID NO: 33, wherein Xaa116 is Ser, Xaa117 is Ala, Xaa118 is Gly, and Xaa119 is Thr. Although in some embodiments, SEQ ID NO: 33 may comprise wild-type CDR3α SEQ ID NO: 5, preferably, SEQ ID NO: 33 does not comprise SEQ ID NO: 5. SEQ ID NO: 34 generally corresponds to positions 1-313 of the native, unsubstituted SEQ ID NO: 12 with the exception that in SEQ ID NO: 34, one or more of one or more of Arg115, Thr116, Gly117, and Pro118 is substituted. Although in some embodiments, SEQ ID NO: 34 may comprise wild-type CDR3β SEQ ID NO: 8, preferably, SEQ ID NO: 34 does not comprise SEQ ID NO: 8.

Like the TCRs of the invention, the functional variants described herein comprise two polypeptide chains, each of which comprises a variable region comprising a CDR1, a CDR2, and a CDR3 of a TCR. Preferably, the first polypeptide chain comprises a CDR1 comprising the amino acid sequence of SEQ ID NO: 3 (CDR1 of α chain), a CDR2 comprising the amino acid sequence of SEQ ID NO: 4 (CDR2 of α chain), and a substituted CDR3 comprising the amino acid sequence of SEQ ID NO: 29 (substituted CDR3 of α chain), and the second polypeptide chain comprises a CDR1 comprising the amino acid sequence of SEQ ID NO: 6 (CDR1 of β chain), a CDR2 comprising the amino acid sequence of SEQ ID NO: 7 (CDR2 of β chain), and a CDR3 comprising the amino acid sequence of SEQ ID NO: 8 (CDR3 of β chain). In another embodiment, the first polypeptide chain comprises a CDR1 comprising the amino acid sequence of SEQ ID NO: 3 (CDR1 of α chain), a CDR2 comprising the amino acid sequence of SEQ ID NO: 4 (CDR2 of α chain), and a CDR3 comprising the amino acid sequence of SEQ ID NO: 5 (CDR3 of α chain), and the second polypeptide chain comprises a CDR1 comprising the amino acid sequence of SEQ ID NO: 6 (CDR1 of β chain), a CDR2 comprising the amino acid sequence of SEQ ID NO: 7 (CDR2 of β chain), and a substituted CDR3 comprising the amino acid sequence of SEQ ID NO: 30 (substituted CDR3 of β chain). In this regard, the inventive functional variant of a TCR can comprise the amino acid sequences selected from the group consisting of SEQ ID NOs: 3-5; SEQ ID NOs: 3-4 and 29; SEQ ID NOs: 6-8; and SEQ ID NOs: 6-7 and 30. Preferably the functional variant of a TCR comprises the amino acid sequences of SEQ ID NOs: 3-4, 29, and 6-8; SEQ ID NOs: 3-7 and 30; or SEQ ID NOs: 3-4, 29, 6-7, and 30. More preferably, the functional variant of a TCR comprises the amino acid sequences of SEQ ID NOs: 3-4, 29, and 6-8.

Alternatively or additionally, the functional variant of a TCR can comprise a substituted amino acid sequence of a variable region of a TCR comprising the CDRs set forth above. In this regard, the TCR can comprise the substituted amino acid sequence of SEQ ID NO: 31 (the substituted variable region of an α chain), 10 (the variable region of a β chain), both SEQ ID NOs: 31 and 10, the substituted amino acid sequence of SEQ ID NO: 32 (the substituted variable region of an β chain), 9 (the variable region of an α chain), both SEQ ID NOs: 9 and 32, or both SEQ ID NOs: 31 and 32. Preferably, the inventive functional variant of a TCR comprises the amino acid sequences of SEQ ID NOs: 31 and 10 or SEQ ID NOs: 32 and 9. More preferably, the inventive functional variant of a TCR comprises the amino acid sequences of SEQ ID NOs: 31 and 10.

Alternatively or additionally, the functional variant of a TCR can comprise a substituted α chain of a TCR and a β chain of a TCR. Each of the α chain and β chain of the inventive TCR can independently comprise any amino acid sequence. Preferably, the substituted α chain comprises a substituted variable region of an α chain as set forth above. In this regard, the inventive substituted α chain of the TCR can comprise the amino acid sequence of SEQ ID NO: 33. An inventive substituted α chain of this type can be paired with any β chain of a TCR. Preferably, the β chain of the inventive TCR comprises the variable region of a β chain as set forth above. In this regard, the inventive TCR can comprise the amino acid sequence of SEQ ID NO: 12 or the substituted amino acid sequence SEQ ID NO: 34. An inventive substituted β chain of this type can be paired with any α chain of a TCR. In this regard, the inventive TCR can comprise the amino acid sequence of SEQ ID NO: 11 or 33. The inventive functional variant of a TCR, therefore, can comprise the amino acid sequence of SEQ ID NO: 11, 12, 33, 34, both SEQ ID NOs: 33 and 34; both SEQ ID NOs: 11 and 34; or both SEQ ID NOs: 12 and 33. Preferably, the inventive functional variant of a TCR comprises the amino acid sequences of SEQ ID NOs: 11 and 34 or SEQ ID NOs: 12 and 33. More preferably, the functional variant of a TCR comprises the amino acid sequences of SEQ ID NOs: 12 and 33.

In an embodiment of the invention, the TCR (or functional variant thereof) may comprise a human constant region. In this regard, the TCR (or functional variant thereof) can comprise a human constant region comprising SEQ ID NO: 23 or 35 (human constant region of an α chain), SEQ ID NO: 24 or 36 (human constant region of β chain), both SEQ ID NOs: 23 and 24, or both SEQ ID NOs: 35 and 36. Preferably, the TCR (or functional variant thereof) comprises both SEQ ID NOs: 23 and 24.

In another embodiment of the invention, the TCR (or functional variant thereof) can comprise a human/mouse chimeric TCR (or functional variant thereof). In this regard, the TCR (or functional variant thereof) can comprise a mouse constant region comprising SEQ ID NO: 25 (mouse constant region of an α chain), SEQ ID NO: 26 (mouse constant region of β chain), or both SEQ ID NOs: 25 and 26. Preferably, the TCR (or functional variant thereof) comprises both SEQ ID NOs: 25 and 26.

The inventive human/mouse chimeric TCR (or functional variant or functional portion thereof) can comprise any of the CDRs set forth above. In this regard, the inventive human/mouse chimeric TCR (or functional variant or functional portion thereof) can comprise the amino acid sequences selected from the group consisting of SEQ ID NOs: 3-5; SEQ ID NOs: 13-15; SEQ ID NOs: 16-18; SEQ ID NOs: 3-4 and 29; SEQ ID NOs: 6-8; and SEQ ID NOs: 6-7 and 30. Preferably the human/mouse chimeric TCR (or functional variant or functional portion thereof) comprises the amino acid sequences of SEQ ID NOs: 3-8; SEQ ID NOs: 13-18; SEQ ID NOs: 3-4, 29, and 6-8; SEQ ID NOs: 3-7 and 30; or SEQ ID NOs: 3-4, 29, 6-7, and 30. More preferably, the human/mouse chimeric TCR (or functional variant or functional portion thereof) comprises the amino acid sequences of SEQ ID NOs: 3-4, 29, and 6-8 or SEQ ID NOs: 3-8.

Alternatively or additionally, the human/mouse chimeric TCR (or functional variant or functional portion thereof) can comprise any of the variable regions set forth above. In this regard, the inventive human/mouse chimeric TCR (or functional variant or functional portion thereof) can comprise the substituted amino acid sequence of SEQ ID NO: 31 (the substituted variable region of an α chain), SEQ ID NO: 10 or 20 (the variable region of a β chain), the substituted amino acid sequence of SEQ ID NO: 32 (the substituted variable region of an β chain), SEQ ID NO: 9 or 19 (the variable region of an α chain), both SEQ ID NOs: 9 and 32, both SEQ ID NOs: 31 and 32, both SEQ ID NOs: 31 and 10, both SEQ ID NOs: 9 and 10, or both SEQ ID NOs: 19 and 20. Preferably, the inventive human/mouse chimeric TCR (or functional variant or functional portion thereof) comprises the amino acid sequences of SEQ ID NOs: 31 and 10, SEQ ID NOs: 9 and 10, or SEQ ID NOs: 32 and 9. More preferably, the inventive functional variant or functional portion of a TCR comprises the amino acid sequences of SEQ ID NOs: 31 and 10 or SEQ ID NOs: 9 and 10.

Alternatively or additionally, the human/mouse chimeric TCR (or functional variant or functional portion thereof) can comprise an α chain of a TCR (or functional variant or functional portion thereof) and a β chain of a TCR (or functional variant or functional portion thereof). Each of the α chain and β chain of the inventive human/mouse chimeric TCR (or functional variant or functional portion thereof) can independently comprise any amino acid sequence. Preferably, the α chain comprises the variable region of an α chain as set forth above. In this regard, the inventive human/mouse chimeric TCR (or functional variant or functional portion thereof) can comprise the amino acid sequence of SEQ ID NO: 27. An inventive human/mouse chimeric TCR (or functional variant or functional portion thereof) of this type can be paired with any β chain of a TCR (or functional variant or functional portion thereof). Preferably, the β chain of the inventive human/mouse chimeric TCR (or functional variant or functional portion thereof) comprises the variable region of a β chain as set forth above. In this regard, the inventive human/mouse chimeric TCR (or functional variant or functional portion thereof) can comprise the amino acid sequence of SEQ ID NO: 28. The inventive human/mouse chimeric TCR (or functional variant or functional portion thereof), therefore, can comprise the amino acid sequence of SEQ ID NO: 27 or 28, or both SEQ ID NOs: 27 and 28. Preferably, the inventive TCR comprises the amino acid sequences of SEQ ID NOs: 27 and 28.

Also provided by the invention is a polypeptide comprising a functional portion of any of the TCRs or functional variants described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR (or functional variant thereof) of which it is a part, provided that the functional portion specifically binds to MAGE-A3 and/or MAGE-A6. The term "functional portion" when used in reference to a TCR (or functional variant thereof) refers to any part or fragment of the TCR (or functional variant thereof) of the invention, which part or fragment retains the biological activity of the TCR (or functional variant thereof) of which it is a part (the parent TCR or parent functional variant thereof). Functional portions encompass, for example, those parts of a TCR (or functional variant thereof) that retain the ability to specifically bind to MAGE-A3 (e.g., in an FILA-DPβ1*04-dependent manner) or MAGE-A6, or detect, treat, or prevent cancer, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR (or functional variant thereof).

The functional portion can comprise additional amino acids at the amino or carboxy terminus of the portion, or at both termini, which additional amino acids are not found in the amino acid sequence of the parent TCR or functional variant thereof. Desirably, the additional amino acids do not interfere with the biological function of the functional portion, e.g., specifically binding to MAGE-A3 and/or MAGE-A6; and/or having the ability to detect cancer, treat or prevent cancer, etc. More desirably, the additional amino acids enhance the biological activity, as compared to the biological activity of the parent TCR or functional variant thereof.

The polypeptide can comprise a functional portion of either or both of the α and β chains of the TCRs or functional variant thereof of the invention, such as a functional portion comprising one of more of CDR1, CDR2, and CDR3 of the variable region(s) of the α chain and/or β chain of a TCR or functional variant thereof of the invention. In this regard, the polypeptide can comprise a functional portion comprising the amino acid sequence of SEQ ID NO: 3 or 13 (CDR1 of α chain), 4 or 14 (CDR2 of α chain), 5, 15, or 29 (CDR3 of α chain), 6 or 16 (CDR1 of β chain), 7 or 17 (CDR2 of β chain), 8, 18, or 30 (CDR3 of β chain), or a combination thereof. Preferably, the inventive polypeptide comprises a functional portion comprising SEQ ID NOs: 3-5; 3-4 and 29; 6-8; 6-7 and 30; 13-15; 16-18; all of SEQ ID NOs: 3-8; all of SEQ ID NOs: 13-18; all of SEQ ID NOs: 3-4, 29, and 6-8; all of SEQ ID NOs: 3-7 and 30; or all of SEQ ID NOs: 3-4, 29, 6-7, and 30. More preferably, the polypeptide comprises a functional portion comprising the amino acid sequences of all of SEQ ID NOs: 3-8 or all of SEQ ID NOs: 3-4, 29, and 6-8.

Alternatively or additionally, the inventive polypeptide can comprise, for instance, the variable region of the inventive TCR or functional variant thereof comprising a combination of the CDR regions set forth above. In this regard, the polypeptide can comprise the amino acid sequence of SEQ ID NO: 9, 19, or 31 (the variable region of an α chain), SEQ ID NO: 10, 20, or 32 (the variable region of a β chain), both SEQ ID NOs: 9 and 10, both SEQ ID NOs: 19 and 20; both SEQ ID NOs: 31 and 32; both SEQ ID NOs: 9 and 32; or both SEQ ID NOs: 10 and 31. Preferably, the polypeptide comprises the amino acid sequences of both SEQ ID NOs: 9 and 10 or both SEQ ID NOs: 10 and 31.

Alternatively or additionally, the inventive polypeptide can comprise the entire length of an α or β chain of one of the TCRs or functional variant thereof described herein. In this regard, the inventive polypeptide can comprise an amino acid sequence of SEQ ID NOs: 11, 12, 21, 22, 27, 28, 33, or 34. Alternatively, the polypeptide of the invention can comprise α and β chains of the TCRs or functional variants thereof described herein. For example, the inventive polypeptide can comprise the amino acid sequences of both SEQ ID NOs: 11 and 12, both SEQ ID NOs: 21 and 22, both SEQ ID NOs: 33 and 34, both SEQ ID NOs: 11 and 34, both SEQ ID NOs: 12 and 33, or both SEQ ID NOs: 27 and 28. Preferably, the polypeptide comprises the amino acid sequences of both SEQ ID NOs: 11 and 12, both SEQ ID NOs: 33 and 12, or both SEQ ID NOs: 27 and 28.

The invention further provides a protein comprising at least one of the polypeptides described herein. By "protein" is meant a molecule comprising one or more polypeptide chains.

In an embodiment, the protein of the invention can comprise a first polypeptide chain comprising the amino acid sequences of SEQ ID NOs: 3-5, SEQ ID NOs: 13-15, or SEQ ID NOs: 3-4 and 29 and a second polypeptide chain comprising the amino acid sequence of SEQ ID NOs: 6-8, SEQ ID NOs: 16-18, or SEQ ID NOs: 6-7 and 30. Alternatively or additionally, the protein of the invention can comprise a first polypeptide chain comprising the amino acid sequence of SEQ ID NO: 9, 19, or 31 and a second polypeptide chain comprising the amino acid sequence of SEQ ID NO: 10, 20, or 32. The protein of the invention can, for example, comprise a first polypeptide chain comprising the amino acid sequence of SEQ ID NO: 11, 21, 27, or 33 and a second polypeptide chain comprising the amino acid sequence of SEQ ID NO: 12, 22, 28, or 34. In this instance, the protein of the invention can be a TCR. Alternatively, if, for example, the protein comprises a single polypeptide chain comprising SEQ ID NO: 11, 21, 27, or 33 and SEQ ID NO: 12, 22, 28, or 34, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

In some embodiments of the invention, the TCRs (and functional portions and functional variants thereof), polypeptides, and proteins of the invention may be expressed as a single protein comprising a linker peptide linking the α chain and the β chain. In this regard, the TCRs (and functional variants and functional portions thereof), polypeptides, and proteins of the invention comprising SEQ ID NO: 11, 21, 27, or 33 and SEQ ID NO: 12, 22, 28, or 34 may further comprise a linker peptide. The linker peptide may advantageously facilitate the expression of a recombinant TCR (including functional portions and functional variants thereof), polypeptide, and/or protein in a host cell. Upon expression of the construct including the linker peptide by a host cell, the linker peptide may be cleaved, resulting in separated α and β chains.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

The TCR (or functional variant thereof), polypeptide, or protein can consist essentially of the specified amino acid sequence or sequences described herein, such that other components of the TCR (or functional variant thereof), polypeptide, or protein, e.g., other amino acids, do not materially change the biological activity of the TCR (or functional variant thereof), polypeptide, or protein. In this regard, the inventive TCR (or functional variant thereof), polypeptide, or protein can, for example, consist essentially of the amino acid sequence of SEQ ID NO: 11, 12, 21, 22, 27, 28, 33, and 34, both SEQ ID NOs: 11 and 12, both SEQ ID NOs: 21 and 22, both SEQ ID NOs: 27 and 28, both SEQ ID NOs: 33 and 34, both SEQ ID NOs: 11 and 34, or both SEQ ID NOs: 12 and 33. Also, for instance, the inventive TCRs (including functional variants thereof), polypeptides, or proteins can consist essentially of the amino acid sequence(s) of SEQ ID NO: 9, 10, 19, 20, 31, 32, both SEQ ID NOs: 9 and 10, both SEQ ID NOs: 19 and 20, both SEQ ID NOs: 31 and 32, both SEQ ID NOs: 9 and 32, both SEQ ID NOs: 10 and 31. Furthermore, the inventive TCRs (including functional variants thereof), polypeptides, or proteins can consist essentially of the amino acid sequence of SEQ ID NO: 3 or 13 (CDR1 of α chain), SEQ ID NO: 4 or 14 (CDR2 of α chain), SEQ ID NO: 5, 15, or 29 (CDR3 of α chain), SEQ ID NO: 6 or 16 (CDR1 of β chain), SEQ ID NO: 7 or 17 (CDR2 of β chain), SEQ ID NO: 8, 18, or 30 (CDR3 of β chain), or any combination thereof, e.g., SEQ ID NOs: 3-5; 6-8; 3-8; 13-15; 16-18; 13-18; 3-4 and 29; 6-7 and 30; 3-4, 29, and 6-8; 3-7 and 30; or 3-4, 29, 6-7, and 30.

The TCRs, polypeptides, and proteins of the invention (including functional variants thereof) can be of any length, i.e., can comprise any number of amino acids, provided that the TCRs, polypeptides, or proteins (or functional variants thereof) retain their biological activity, e.g., the ability to specifically bind to MAGE-A3 and/or MAGE-A6; detect cancer in a mammal; or treat or prevent cancer in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional variants thereof) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional variants thereof) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention (including functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the TCRs, polypeptides, and proteins of the invention (including functional variants thereof) can be isolated and/or purified from a source, such as a plant, a bacterium, an insect, a mammal, e.g., a rat, a human, etc. Methods of isolation and purification are well-known in the art. Alternatively, the TCRs, polypeptides, and/or proteins described herein (including functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs (including functional variants thereof), polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, proteins, or functional variants thereof described herein. For example, the nucleic acid can comprise, consist, or consist essentially of any one or more of the nucleotide sequence SEQ ID NOs: 37-44.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs (including functional portions and functional variants thereof). It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2 μ plasmid, λ, SV40, bovine papilloma virus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein (including functional variants thereof), or to the nucleotide sequence which is complementary to or which hybridizes to the nucleotide sequence encoding the TCR, polypeptide, or protein (including functional variants thereof). The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the *thymus*, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, CD4+ T cells, $CD8^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The invention further provides an antibody, or antigen binding portion thereof, which specifically binds to a functional portion of any of the TCRs (or functional variant thereof) described herein. Preferably, the functional portion specifically binds to the cancer antigen, e.g., the functional portion comprising the amino acid sequence SEQ ID NO: 3 or 13 (CDR1 of α chain), 4 or 14 (CDR2 of α chain), 5, 15, or 29 (CDR3 of α chain), 6 or 16 (CDR1 of β chain), 7 or 17 (CDR2 of β chain), 8, 18, or 30 (CDR3 of β chain), SEQ ID NO: 9, 19, or 31 (variable region of α chain), SEQ ID NO: 10, 20, or 32 (variable region of β chain), or a combination thereof, e.g., 3-5; 6-8; 3-8; 13-15; 16-18; 13-18; 3-4 and 29; 6-7 and 30; 3-4, 29, and 6-8; or 3-7 and 30; 3-4, 29, 6-7, and 30. More preferably, the functional portion comprises the amino acid sequences of SEQ ID NOs: 3-8 or SEQ ID NOs: 3-4, 29, and 6-8. In a preferred embodiment, the antibody, or antigen binding portion thereof, binds to an epitope which is formed by all 6 CDRs (CDR1-3 of the alpha chain and CDR1-3 of the beta chain). The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR (or functional variant thereof). Desirably, the antibody is specific for the functional portion of the inventive TCR (or functional variants thereof), such that there is minimal cross-reaction with other peptides or proteins.

Methods of testing antibodies for the ability to bind to any functional portion or functional variant of the inventive TCR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. I Immunol.*, 5, 511-519 (1976), Harlow and Lane (eds.), *Antibodies: A Laboratory Manual*, CSH Press (1988), and C. A. Janeway et al. (eds.), *Immunobiology*, $5^{th}$ Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1.

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), *Molecular Cloning A Laboratory Manual*, $3^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in, for example, U.S. Pat. No. 5,639,641 and Pedersen et al., *J. Mol. Biol.*, 235, 959-973 (1994).

The invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, (including functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for oral, aerosol, parenteral, subcutaneous, intravenous, intramuscular, intraarterial, intrathecal, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

In an embodiment of the invention, the pharmaceutical composition may further comprise MHC Class I restricted TCRs, or polypeptides, proteins, nucleic acids, or recombinant expression vectors encoding MHC Class I restricted TCRs, or host cells or populations of cells expressing MHC Class I restricted TCRs. Without being bound to a particular theory, it is believed that MHC Class I restricted CD8+ T cells augment the reactivity of MHC Class II restricted CD4+ T cells and enhance the ability of the MHC Class II restricted CD4+ T cells to treat or prevent cancer.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR (or functional variant or functional portion thereof), polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. In an embodiment in which the inventive TCR material is a population of cells, the number of cells administered per infusion may vary, e.g., from about $1 \times 10^6$ to about $1 \times 10^{11}$ cells or more.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a targeting moiety. The practice of conjugating compounds, e.g., inventive TCR materials, to targeting moieties is known in the art. See, for instance, Wadwa et al., *J Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). The term "bridge" as used herein, refers to any agent or molecule that links the inventive TCR materials to the targeting moiety. One of ordinary skill in the art recognizes that sites on the inventive TCR materials, which are not necessary for the function of the inventive TCR materials, are ideal sites for attaching a bridge and/or a targeting moiety, provided that the bridge and/or targeting moiety, once attached to the inventive TCR materials, do(es) not interfere with the function of the inventive TCR materials, i.e., the ability to bind to MAGE-A3 or MAGE-A6; or to detect, treat, or prevent cancer.

It is contemplated that the inventive pharmaceutical compositions, TCRs (including functional variants thereof), polypeptides, proteins, nucleic acids, recombinant expression vectors, host cells, or populations of cells can be used in methods of treating or preventing cancer. Without being bound to a particular theory, the inventive TCRs (and functional variants thereof) are believed to bind specifically to MAGE-A3 and/or MAGE-A6, such that the TCR (or related inventive polypeptide or protein and functional variants thereof) when expressed by a cell is able to mediate an immune response against a target cell expressing MAGE-A3 or MAGE-A6. In this regard, the invention provides a method of treating or preventing cancer in a mammal, comprising administering to the mammal any of the pharmaceutical compositions, TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a recombinant vector which encodes any of the TCRs (and functional variants thereof), polypeptides, or proteins described herein, in an amount effective to treat or prevent cancer in the mammal.

In an embodiment of the invention, the inventive methods of treating or preventing cancer may further comprise co-administering MHC Class I restricted TCRs, or polypeptides, proteins, nucleic acids, or recombinant expression vectors encoding MHC Class I restricted TCRs, or host cells or populations of cells expressing MHC Class I restricted TCRs, to the mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Also provided is a method of detecting the presence of cancer in a mammal. The method comprises (i) contacting a sample comprising cells of the cancer with any of the inventive TCRs (and functional variants thereof), polypeptides, proteins, nucleic acids, recombinant expression vectors, host cells, populations of cells, or antibodies, or antigen binding portions thereof, described herein, thereby forming a complex, and detecting the complex, wherein detection of the complex is indicative of the presence of cancer in the mammal.

With respect to the inventive method of detecting cancer in a mammal, the sample of cells of the cancer can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs (and functional variants thereof), polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phyco- erythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of sarcomas (e.g., synovial sarcoma, osteogenic sarcoma, leiomyosarcoma uteri, and alveolar rhabdomyosarcoma), lymphomas (e.g., Hodgkin lymphoma and non-Hodgkin lymphoma), hepatocellular carcinoma, glioma, head cancers (e.g., squamous cell carcinoma), neck cancers (e.g., squamous cell carcinoma), acute lymphocytic cancer, leukemias (e.g., acute myeloid leukemia and chronic lymphocytic leukemia), bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic myeloid cancer, colon cancers (e.g., colon carcinoma), esophageal cancer, cervical cancer, gastric cancer, gastrointestinal carcinoid tumor, hypopharynx cancer, larynx cancer, liver cancers (e.g., hepatocellular carcinoma), lung cancers (e.g., non-small cell lung carcinoma), malignant mesothelioma, melanoma, multiple myeloma, nasopharynx cancer, ovarian cancer, pancreatic cancer, peritoneum, omentum, and mesentery cancer, pharynx cancer, prostate cancer, rectal cancer, kidney cancers (e.g., renal cell carcinoma), small intestine cancer, soft tissue cancer, stomach cancer, testicular cancer, thyroid cancer, and urothelial cancers (e.g., ureter cancer and urinary bladder cancer). Preferably, the cancer is melanoma, breast cancer, lung cancer, prostate cancer, synovial cell sarcoma, head and neck cancer, esophageal cancer, or ovarian cancer.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

EXAMPLE 1A

This example demonstrates the isolation of TCRs from T cell clones.

Anti-MAGE-A3$_{243-258}$ CD4+ effector clone R12C9 and anti-MAGE-A3$_{243-258}$ Treg clone 6F9 was cultured with peptide (MAGE-A3$_{243-258}$)-pulsed EBV B cells. Cytokine secretion, percentage of indicator cells suppressed, percentage of FOXP3+ Treg cells, and percentage of unmethylated FOXP3 sequences were measured. Unmethylated FOXP3 intron 1 sequences are considered to be a marker for a stable Treg phenotype. The results for the 6F9 and R12C9 clones are shown in Tables 1A and 1B.

TABLE 1A

| Clone | % Indicator Cells Suppressed | % FOXP3+ | % Unmethylated FOXP3 sequences |
|---|---|---|---|
| 6F9 | 57 | 95 | 72 |
| R12C9 | 0 | 8 | 2 |

TABLE 1B

| | Cytokine Secretion (pg/25,000 cells) | | | | | |
|---|---|---|---|---|---|---|
| Clone | IFN-γ | IL-2 | IL-10 | IL-4 | IL-5 | TNF-α |
| 6F9 | 0 | 0 | 0 | 0 | 0 | 12 |
| R12C9 | 922 | 46 | 479 | 8 | 28 | 422 |

Treg clones can inhibit the proliferation of indicator cells after stimulation by an appropriate peptide. As shown in Table 1A, clone 6F9 is a Treg clone.

A TCR comprising SEQ ID NOs: 21 and 22 was cloned from the anti-MAGE-A3$_{243-258}$ CD4+ effector clone R12C9 ("R12C9 TCR"). A TCR comprising SEQ ID NOs: 11 and 12 was cloned from the anti-MAGE-A3$_{243-258}$ Treg clone 6F9 ("6F9 TCR").

EXAMPLE 1B

This example demonstrates the transduction efficiency of PBMC transduced with a nucleotide sequence encoding the 6F9 TCR or R12C9 TCR of Example 1.

Transcripts encoding the TCR alpha and beta chains of R12C9 and 6F9 were linked with sequences encoding a P2A self-cleaving peptide and cloned into an MSGV1 retroviral vector. PBMC from three patients were stimulated with OKT3, transduced with transient retroviral supernatants on day two, and enriched for CD4+ T cells on day seven. The levels of TCR expression were evaluated by staining transduced cells with anti-Vβ22 or Vβ6.7, which detect the 6F9 or R12C9 TCR, respectively. Analysis of PBMC from patient 1 indicated that between 25 and 35% of the T cells were transduced with the individual TCRs and similar transduction levels were obtained with PBMC from patients 2 and 3.

EXAMPLE 2

This example demonstrates that T cells transduced with nucleotide sequences encoding the anti-MAGE-A3$_{243-258}$ TCRs of Example 1 recognize 293-class II, major histocompatibility complex, transactivator (CIITA) transfectants of MAGE-A3 and peptide-pulsed targets. This example also demonstrates that the 6F9 TCR recognizes 293-CIITA transfectants of MAGE-A3 and MAGE-A6.

CD4+ enriched peripheral blood lymphocytes (PBL) from two human donors were untransduced (UT) or transduced with F5 (anti-MART-1) TCR, R12C9 TCR, or 6F9 TCR. The cells were cultured with 293-CIITA-transfected target cells pulsed with MAGE-A3$_{243-258}$ (SEQ ID NO: 2) peptide. The 293-CIITA cells are 293 cells transduced with CIITA, which is a human gene which encodes the class II, major histocompatibility complex transactivator protein. The results obtained with 6F9 and R12C9 TCR-transduced cells are shown in Table 2 and FIG. 10A. PBL transduced by R12C9 TCR or 6F9 TCR recognized MAGE-A3$_{243-258}$ peptide-pulsed HLA-DP*0401+ target cells. Titration of the MAGE-A3$_{243-258}$ peptide indicated that CD4+ T cells transduced with the 6F9 or R12C9 TCRs released comparable levels of IFN-γ in response to targets pulsed with a minimum of between 0.001 and 0.01 mg/ml of the MAGE-A3:$_{243-258}$ peptide. The experiments were repeated using PBL from a third human donor and similar results were obtained.

TABLE 2

| | | IFN-gamma (pg/ml) | |
|---|---|---|---|
| DP4+ | Peptide (µg/ml) | Untransduced (UT) | 6F9 TCR transduced |
| | Donor 1 | | |
| 293-CIITA + MAGE-A3$_{243-258}$ | 0.0001 | 2 | 328 |
| | 0.001 | 17 | 596 |
| | 0.01 | 4 | 1609 |
| | 0.1 | 2 | 7440 |
| | 1 | 4 | 34800 |
| | 10 | 0 | 52100 |
| | Donor 2 | | |
| 293-CIITA + MAGE-A3$_{243-258}$ | 0.0001 | 28 | 110 |
| | 0.001 | 30 | 323 |
| | 0.01 | 37 | 1830 |
| | 0.1 | 40 | 9760 |
| | 1 | 44 | 55000 |
| | 10 | 0 | 59050 |

293-CIITA target cells were transfected with DNA constructs (pCDNA3 vector) encoding full-length MAGE-A3 protein or MAGE-A6 protein, which differ at only a single position (249), or full-length MAGE-A1 protein or MAGE-A12 protein. Untransduced and transduced PBL were co-cultured with the transfected 293-CIITA cells and interferon (IFN) gamma secretion was measured. The results are shown in FIGS. 1A, 1B, and 10A.

Figure 1:
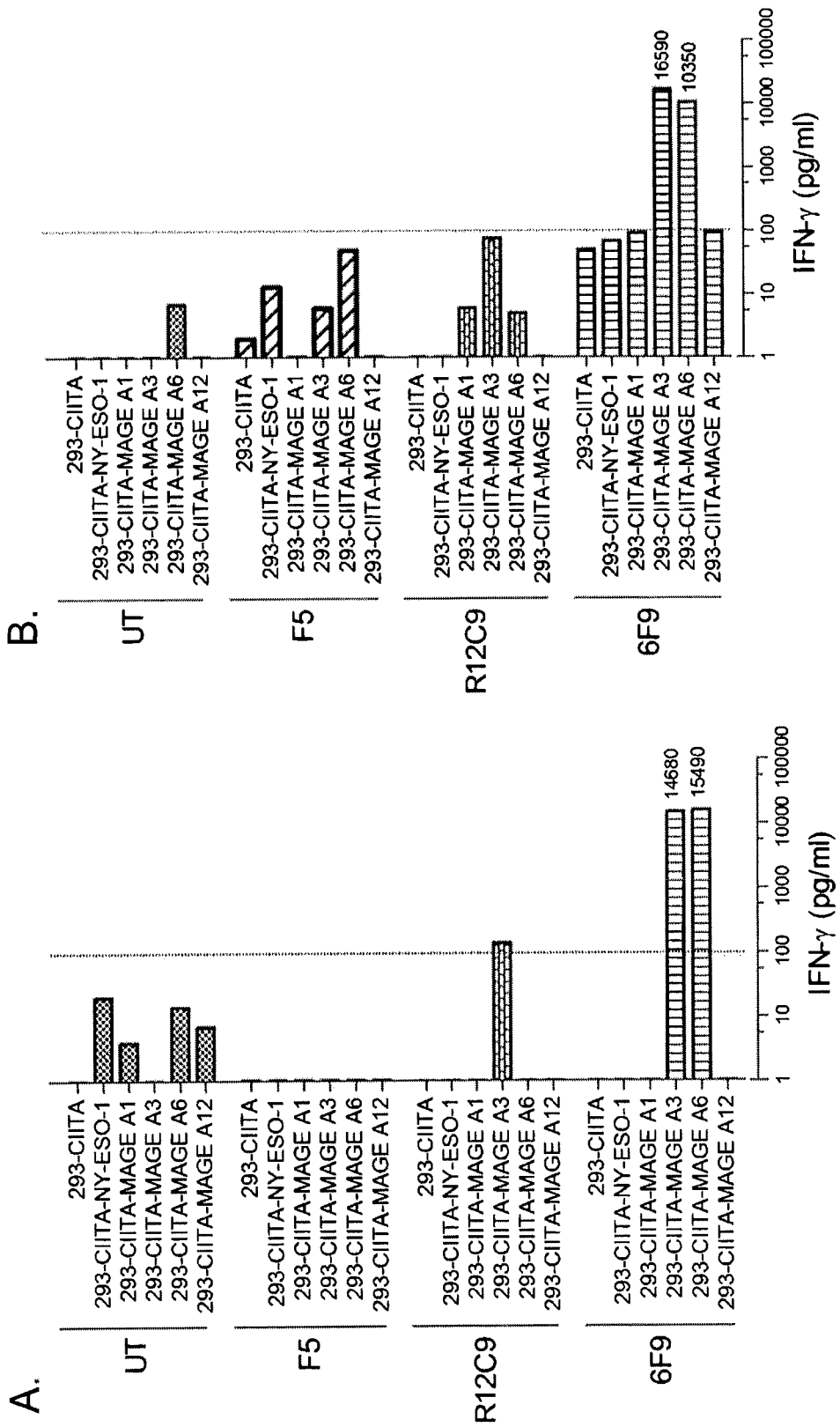

As shown in FIGS. 1A, 1B, and 10A, although T cells transduced with R12C9 TCR or 6F9 TCR recognized peptide-pulsed targets, PBL transduced with the 6F9 TCR were the most highly reactive to each of MAGE-A3 and MAGE-A6 293-CIITA transfectants. CD4+ T cells transduced with the 6F9 but not the R12C9 TCR recognized HLA DP*0401+ 293-CIITA cells transfected with genes encoding MAGE-A3 or MAGE-A6, but not MAGE-A1 or A12. Comparison of amino acid sequences of the corresponding regions of the MAGE family members indicated that MAGE-A3 and MAGE-A6 only differed at one position (residue 249), whereas the other MAGE family members differed from MAGE-A3 at two (MAGE-A12$_{243-258}$ (SEQ ID NO: 70)) or three (MAGE-A1$_{243-258}$ (SEQ ID NO: 71)) positions. In addition, CD4+ T cells transduced with the 6F9 TCR but not the R12C9 TCR recognized the MAGE-A3+/HLA-DP*0401+ melanoma cell line 1359 mel-CIITA but failed to recognize the MAGE-A3+/HLA-DP*0401− melanoma cell line 624 mel-CIITA. CD4+ T cells transduced with the R12C9 TCR failed to recognize either of the tested melanoma cell lines. Cells transduced with the MART-1 reactive TCR DMF5 failed to recognize the transfected 293-CIITA cells or MAGE-A3:$_{243-258}$ pulsed target cells, but recognized the HLA-A*0201+ and MART-1+ cell line 624 mel-CIITA. The experiments were repeated using PBL from a third human donor and similar results were obtained. Because the 6F9 TCR was obtained from a Treg clone, which are involved in the suppression of immune activity, the reactivity of the 6F9 TCR was surprising and unexpected. These results indicated that while CD4+ T cells transduced with 6F9 or R12C9 recognized peptide pulsed target cells, only cells transduced with the 6F9 TCR recognized transfected target cells as well as MAGE-A3+ and HLA-DP*04+ tumor cells.

EXAMPLE 3

This example demonstrates that 6F9-transduced PBLs show high reactivity to MAGE-A3 full-length protein processed and presented by HLA-DP4+ B cells.

PBL from two human donors was untransduced or transduced with a nucleotide sequence encoding the 6F9 TCR. The cells were co-cultured with HLA-DP4+ B cells that had processed and presented full-length MAGE-A3 protein (SEQ ID NO: 1). The results are shown in Table 3 and FIG. 10A. As shown in Table 3 and FIG. 10A, the 6F9-transduced PBLs were highly reactive to MAGE-A3 full-length protein processed and presented by HLA-DP4+ B cells.

TABLE 3

| | DP4 | MAGE-A3 (µg/ml) | IFN-γ (pg/ml) Untransduced (UT) | 6F9 TCR transduced |
|---|---|---|---|---|
| | | Donor 1 | | |
| B cells + | + | 10 | 360 | 23640 |
| MAGE-A3 | + | 1 | 420 | 12440 |
| full length | + | 0.1 | 358 | 2360 |
| | + | 0.01 | 362 | 580 |
| | + | 0.001 | 343 | 427 |
| | + | 0.0001 | 349 | 387 |
| | + | 0 | 343 | 405 |
| B cells + NY-ESO-1 full length | + | 10 | 313 | 363 |
| | | Donor 2 | | |
| B cells + | + | 10 | 2080 | 63100 |
| MAGE-A3 | + | 1 | 1810 | 21270 |
| full length | + | 0.1 | 1382 | 3590 |
| | + | 0.01 | 1519 | 685 |
| | + | 0.001 | 1297 | 470 |
| | + | 0.0001 | 1568 | 542 |
| | + | 0 | 1351 | 404 |
| B cells + NY-ESO-1 full length | + | 10 | 1549 | 530 |

EXAMPLE 4

This example demonstrates that 6F9 TCR-transduced PBLs are reactive to tumor lines with endogenous class II presentation of MAGE-A3 protein.

PBL from two human donors were untransduced or transduced with a nucleotide sequence encoding the 6F9 TCR or F5 TCR. The cells were cultured alone (T cell only) or co-cultured with 624-CIITA cells, 526-CIITA cells, or H1299-CIITA cells (tumor cell lines transfected with CIITA). The results are shown in Table 4. As shown in Table 4, 6F9 TCR-transduced PBLs were reactive to tumor lines with endogenous class II presentation of MAGE-A3 protein.

TABLE 4

| | DP4 | MAGE A3 | IFN-gamma (pg/ml) Untransduced | F5 transduced | 6F9 transduced |
|---|---|---|---|---|---|
| | | Donor 1 | | | |
| 624-CIITA | − | + | 223 | 1483 | 238 |
| 526-CIITA | + (DP4 0401) | + | 636 | 2360 | 1314 |
| H1299-CIITA | + (DP4 0401) | + | 284 | 243 | 4330 |
| T-cell only | | | 131 | 45 | 112 |
| | | Donor 2 | | | |
| 624-CIITA | − | + | 819 | 1435 | 153 |
| 526-CIITA | + | + | 117 | 2530 | 1339 |
| H1299-CIITA | + | + | 147 | 172 | 3630 |
| T-cell only | | | 65 | 27 | 88 |

EXAMPLE 5

This example demonstrates that the 6F9 TCR is MAGE-A3 specific.

PBL from a human donor were CD4+ enriched and the number of cells was rapidly expanded on day 27. Cells were untransduced or transduced with F5 TCR or 6F9 TCR and co-cultured with 526-CIITA cells or H1299-CIITA cells alone or with anti-MAGE-A3 siRNA or anti-MART-1 siRNA. IFN-gamma secretion was measured. The results are shown in FIGS. 2A and 2B.

Figure 2:
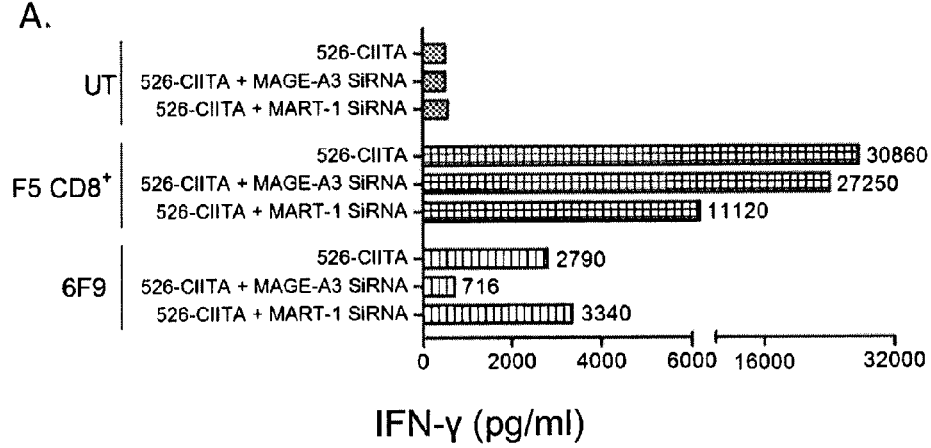
FIG. 2A is a bar graph showing IFN-gamma secretion (pg/ml) by T cells from a human donor that were untransduced or transduced with 6F9 TCR or F5 TCR in response to co-culture with 526-CIITA cells that were untreated or treated with anti-MAGE-A3 siRNA or anti-MART-1 siRNA.
FIG. 2B is a bar graph showing IFN-gamma secretion (pg/ml) by CD4+ T cells from a human donor that were untransduced or transduced with 6F9 TCR in response to co-culture with H1299-CIITA cells that were untreated or treated with anti-MAGE-A3 siRNA or anti-MART-1 siRNA.
Figure 2:
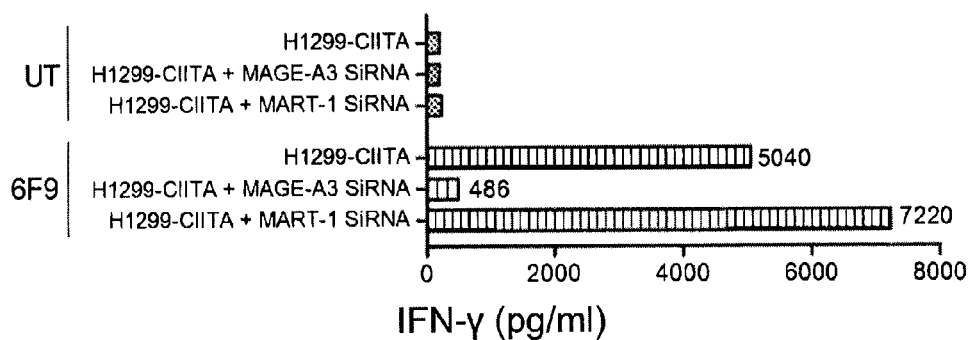

As shown in FIGS. 2A and 2B, the anti-MAGE-A3 siRNA reduced the reactivity of the 6F9-TCR transduced cells. Accordingly, the siRNA knockdown assay confirmed that the 6F9 TCR is MAGE-A3 specific.

EXAMPLE 6

This example demonstrates that 6F9 TCR recognizes MAGE-A3 in an HLA-DP restricted manner.

624, 526, 1359, H1299, 1300, 1764, 3071, 397, 2630, and 2984 tumor cell lines were transduced with CIITA (624-CIITA, 526-CIITA, 1359-CIITA, H1299-CIITA, 1300-CIITA, 1764-CIITA, 3071-CIITA, 397-CIITA, 2630-CIITA, and 2984-CIITA) and HLA-DP expression was measured by flow cytometry. DP4 and MAGE-A3 expression is shown in Table 5A.

TABLE 5A

| Transduced Tumor Cell Line | DP4 | MAGE-A3 |
|---|---|---|
| 624-CIITA | — | + |
| 1300-CIITA | — | + |
| 3071-CIITA | 0402 | + |
| Whitington-CIITA | 0401 | − |
| 526-CIITA | 0401 | + |
| 1359-CIITA | 0401 | + |
| H1299-CIITA | 0401 | + |
| 397-CIITA | 0401 | + |
| 2630-CIITA | 0401 | + |
| 2984-CIITA | 0401 | + |

6F9-transduced PBL were cultured alone (T cells only) or co-cultured with 3071 cells, 3071-CIITA cells, 397 cells, 397-CIITA cells, 2630 cells, 2630-CIITA cells, 2984 cells, and 2984-CIITA cells. IFN-gamma secretion was measured.

Figure 3:
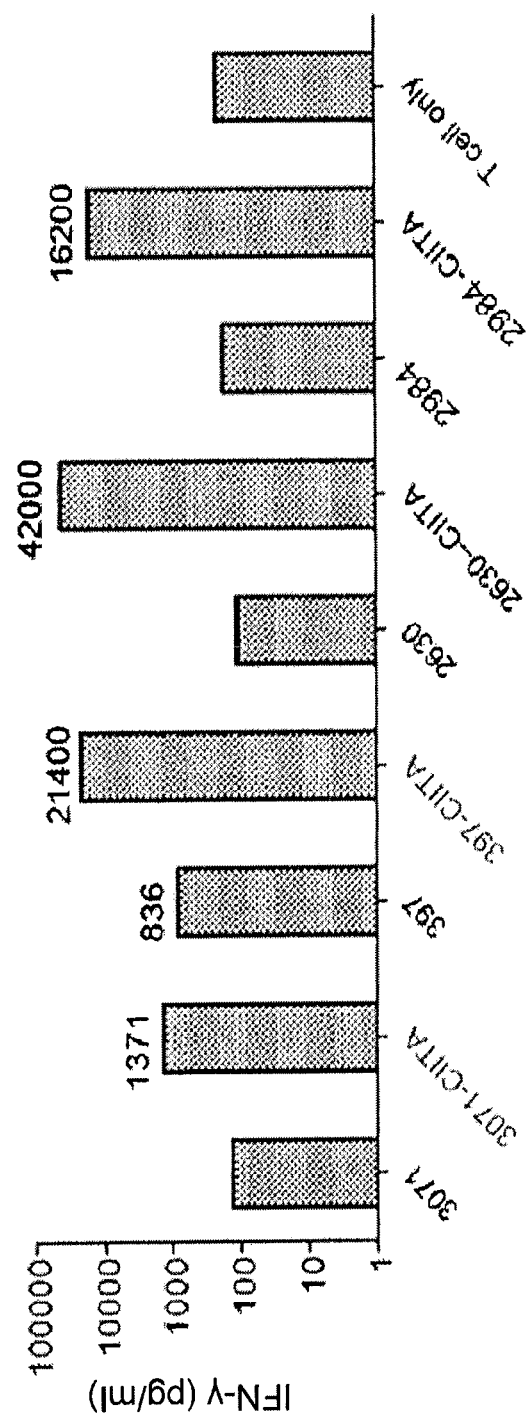
FIG. 3 is a bar graph showing IFN-gamma secretion (pg/ml) by 6F9-transduced PBL cultured alone (T cells only) or co-cultured with 3071 cells, 3071-CIITA cells, 397 cells, 397-CIITA cells, 2630 cells, 2630-CIITA cells, 2984 cells, or 2984-CIITA cells.

The results are shown in FIG. 3. As shown in FIG. 3, 6F9-transduced PBL were reactive with CIITA-expressing tumor cell lines.

The 6F9 TCR was further evaluated by determining the reactivity of CD4+ and CD8+ T cells separated from two patient PBMCs against a panel of tumor cell lines including 624-CIITA, 526-CIITA, 1359-CIITA, H1299-CIITA, SK37-CIITA, 1764-CIITA, 3071-CIITA, 397-CIITA, 2630-CIITA, and 2984-CIITA. Five melanoma cell lines that expressed MAGE-A3 and HLA-DP*0401 (2630-CIITA, 397-CIITA, 2984-CIITA, 526-CIITA, and 1359-CIITA), as well as the non-small cell lung carcinoma cell line H1299 NSCLC-CIITA were recognized by transduced CD4+ and CD8+ T cells, although CD4+ T cells secreted higher amounts of cytokine in response to tumor targets than transduced CD8+ T cells.

H1299-CIITA and 526-CIITA cells were transfected with anti-HLA-DP or anti-HLA-DR siRNA to knock down HLA-DP or HLA-DR expression. 3071-CIITA and 526-CIITA cells were transfected with anti-HLA-DQ siRNA to knock down HLA-DQ expression. HLA-DP, HLA-DR, or HLA-DQ knockout was confirmed by flow cytometry.

Figure 4:
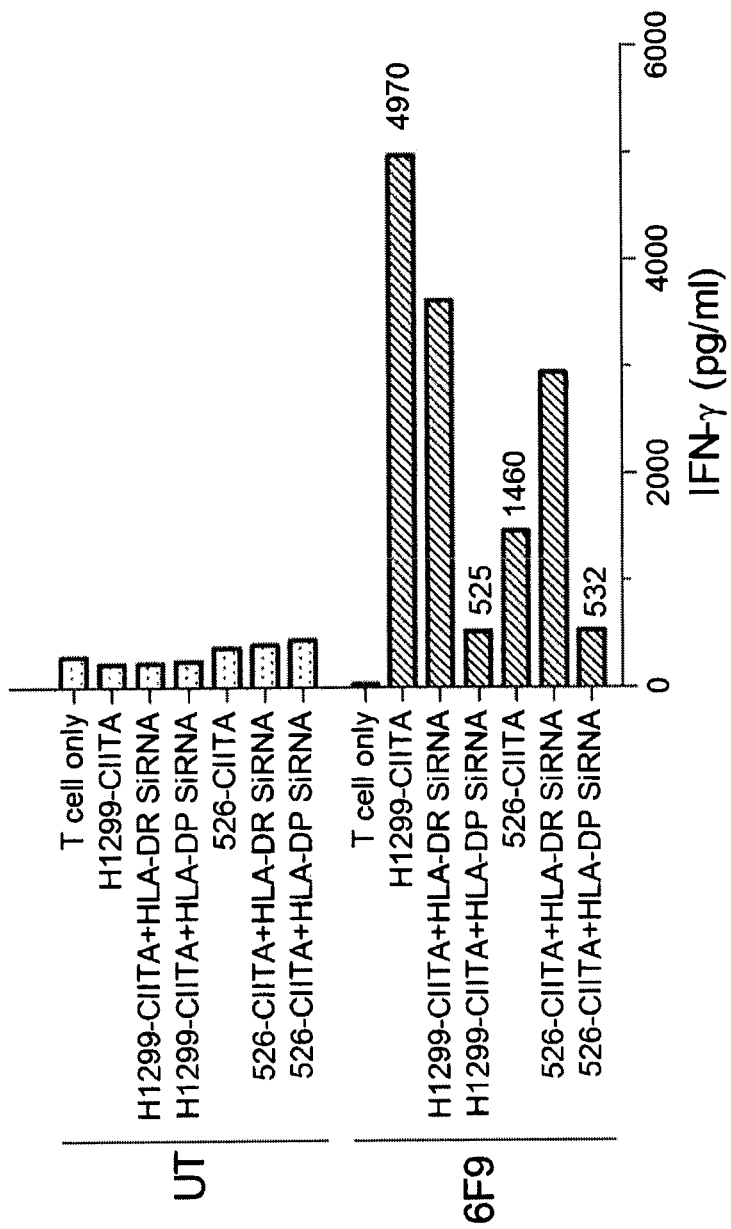
FIG. 4 is a bar graph showing IFN-gamma secretion (pg/ml) by CD4+ enriched PBL that were transduced with 6F9 TCR or untransduced upon culture alone (T cell only) or in response to co-culture with untreated H1299-CIITA cells, H1299-CIITA transfected with anti-HLA-DP or anti-HLA-DR siRNA, untreated 526-CIITA cells, or 526-CIITA transfected with anti-HLA-DP or anti-HLA-DR siRNA.

PBL from a human donor were enriched for CD4+ and the number of cells was rapidly expanded on day 30. The cells were transduced with 6F9 TCR or untransduced. The cells were cultured alone (T cell only) or co-cultured with untreated H1299-CIITA cells, H1299-CIITA transfected with anti-HLA-DP or anti-HLA-DR siRNA, untreated 526-CIITA cells, or 526-CIITA transfected with anti-HLA-DP or anti-HLA-DR siRNA. IFN-gamma secretion was measured. The results are shown in FIG. 4. As shown in FIG. 4, the anti-HLA-DP siRNA reduced the reactivity of the 6F9-TCR transduced cells.

Further studies employing antibodies confirmed that the 6F9 TCR recognizes MAGE-A3 in an HLA-class II restricted manner. PBL transduced with 6F9 TCR were co-cultured with the cells set forth in Table 5B and blocked with the antibodies set forth in Table 5B. IFN-gamma was measured, and the results are set forth in Table 5B.

TABLE 5B

| 6F9 TCR-transduced PBL co-cultured with: | Blocked with antibody: | IFN-gamma (pg/ml) |
| --- | --- | --- |
| 293-CIITA (DP4+) transfected with MAGE-A3 gene | W6/32 (α-HLA class I) | >10,000 |
| | HB22 (α-HLA class DR) | >10,000 |
| | IVA12 (α-HLA class II) | 902 |
| Allen B cells (A2+ DP4+) Incubated with MAGE-A3 protein | W6/32 (α-HLA class I) | 15038 |
| | HB22 (α-HLA class DR) | 16599 |
| | IVA12 (α-HLA class II) | 129 |
| SK37 CIITA (A2+ DP4+ MAGE-A3+) | W6/32 (α-HLA class I) | 1965 |
| | HB22 (α-HLA class DR) | 6248 |
| | IVA12 (α-HLA class II) | 674 |
| H1299 CIITA (A2− DP4+ MAGE-A3+) | W6/32 (α-HLA class I) | 2684 |
| | HB22 (α-HLA class DR) | 7888 |
| | IVA12 (α-HLA class II) | 0 |
| 1764 RCC CIITA (A2−DP4+ MAGE-A3−) | W6/32 (α-HLA class I) | 0 |
| | HB22 (α-HLA class DR) | 0 |
| | IVA12 (α-HLA class II) | 0 |

As shown in Table 5B, the antibody blocking studies showed that the 6F9 TCR recognizes MAGE-A3 in an HLA Class II-restricted manner, but not in an HLA-DR-restricted manner or in an HLA Class I-restricted manner.

EXAMPLE 7

This example demonstrates that an alanine substitution at position 116 or 117 of the alpha chain of the 6F9 TCR increases the reactivity of the 6F9 TCR.

Eight different substituted TCRs, each having one alanine substitution at a different location in the CDR3 region of the 6F9 TCR, were prepared as set forth in Table 6.

TABLE 6

| Name | Description | SEQ ID NO: |
| --- | --- | --- |
| a1 | Alanine substitution at position 116 of alpha chain (S116A) | SEQ ID NO: 12 (wild-type (wt) beta chain) SEQ ID NO: 33 (substituted alpha chain), wherein Xaa at 116 is Ala, Xaa at 117 is Ser, Xaa at 118 is Gly, and Xaa at 119 is Thr |
| a2 | Alanine substitution at position 117 of alpha chain (S117A) | SEQ ID NO: 12 (wild-type (wt) beta chain) SEQ ID NO: 33 (substituted alpha chain), wherein Xaa at 116 is Ser, Xaa at 117 is Ala, Xaa at 118 is Gly, and Xaa at 119 is Thr |
| a3 | Alanine substitution at position 118 of alpha chain (G118A) | SEQ ID NO: 12 (wild-type (wt) beta chain) SEQ ID NO: 33 (substituted alpha chain), wherein Xaa at 116 is Ser, Xaa at 117 is Ser, Xaa at 118 is Ala, and Xaa at 119 is Thr |
| a4 | Alanine substitution at position 119 of alpha chain (T119A) | SEQ ID NO: 12 (wild-type (wt) beta chain) SEQ ID NO: 33 (substituted alpha chain), wherein Xaa at 116 is Ser, Xaa at 117 is Ser, Xaa at 118 is Gly, and Xaa at 119 is Ala |
| b1 | Alanine substitution at position 115 of beta chain (R115A) | SEQ ID NO: 11 (wild-type (wt) alpha chain) and SEQ ID NO: 34, wherein Xaa at 115 is Ala, Xaa at 116 is Thr, Xaa at 117 is Gly, and Xaa at 118 is Pro |
| b2 | Alanine substitution at position 116 of beta chain (T116A) | SEQ ID NO: 11 (wild-type (wt) alpha chain) and SEQ ID NO: 34, wherein Xaa at 115 is Arg, Xaa at 116 is Ala, Xaa at 117 is Gly, and Xaa at 118 is Pro |
| b3 | Alanine substitution at position 117 of beta chain (G117A) | SEQ ID NO: 11 (wild-type (wt) alpha chain) and SEQ ID NO: 34, wherein Xaa at 115 is Arg, Xaa at 116 is Thr, Xaa at 117 is Ala, and Xaa at 118 is Pro |
| b4 | Alanine substitution at position 118 of beta chain (P118A) | SEQ ID NO: 11 (wild-type (wt) alpha chain) and SEQ ID NO: 34, wherein Xaa at 115 is Arg, Xaa at 116 is Thr, Xaa at 117 is Gly, and Xaa at 118 is Ala |

PBL from a human donor were untransduced or transduced with wild-type (wt) 6F9 TCR or one of each of the eight substituted TCRs in Table 6. The cells were cultured alone (T cell only) or co-cultured with 624-CIITA, 526-CIITA, 1359-CIITA, H1299-CIITA, or 1764-CIITA. IFN-gamma secretion was measured. The results are set forth in FIG. 5. As shown in FIG. 5, the a1 and a2 substituted TCRs demonstrated increased reactivity as compared to wt 6F9 TCR.

A separate experiment with transduced, CD4+ enriched PBL also confirmed the superior reactivity of the a1 and a2 substituted TCRs (FIG. 6). As shown in FIG. 6, the a1 and a2 substituted TCRs showed an approximately 2-fold increase in anti-tumor activity as compared to wt 6F9 TCR. The a1 and a2 substituted TCRs also showed better tetramer (SEQ ID NO: 2) binding as compared to the wt 6F9 TCR, as measured by flow cytometry.

EXAMPLE 8

This example demonstrates the reactivity of substituted 6F9 TCRs.

Eight different substituted TCRs, each having one amino acid substitution at a different location in the CDR3 region of the alpha chain of the 6F9 TCR, were prepared as set forth in Table 7.

TABLE 7

| Name | Description | SEQ ID NO: |
|---|---|---|
| a1-1 | Leucine substitution at position 116 of alpha chain (S116L) | SEQ ID NO: 12 (wild-type (wt) beta chain) SEQ ID NO: 33 (substituted alpha chain), wherein Xaa at 116 is Leu, Xaa at 117 is Ser, Xaa at 118 is Gly, and Xaa at 119 is Thr |
| a1-2 | Isoleucine substitution at position 116 of alpha chain (S116I) | SEQ ID NO: 12 (wild-type (wt) beta chain) SEQ ID NO: 33 (substituted alpha chain), wherein Xaa at 116 is Ile, Xaa at 117 is Ser, Xaa at 118 is Gly, and Xaa at 119 is Thr |
| a1-3 | Valine substitution at position 116 of alpha chain (S116V) | SEQ ID NO: 12 (wild-type (wt) beta chain) SEQ ID NO: 33 (substituted alpha chain), wherein Xaa at 116 is Val, Xaa at 117 is Ser, Xaa at 118 is Gly, and Xaa at 119 is Thr |
| a1-4 | Methionine substitution at position 116 of alpha chain (S116M) | SEQ ID NO: 12 (wild-type (wt) beta chain) SEQ ID NO: 33 (substituted alpha chain), wherein Xaa at 116 is Met, Xaa at 117 is Ser, Xaa at 118 is Gly, and Xaa at 119 is Thr |
| a2-1 | Leucine substitution at position 117 of beta chain (S117L) | SEQ ID NO: 12 (wild-type (wt) beta chain) SEQ ID NO: 33 (substituted alpha chain), wherein Xaa at 116 is Ser, Xaa at 117 is Leu, Xaa at 118 is Gly, and Xaa at 119 is Thr |
| a2-2 | Isoleucine substitution at position 117 of beta chain (S117I) | SEQ ID NO: 12 (wild-type (wt) beta chain) SEQ ID NO: 33 (substituted alpha chain), wherein Xaa at 116 is Ser, Xaa at 117 is Ile, Xaa at 118 is Gly, and Xaa at 119 is Thr |
| a2-3 | Valine substitution at position 117 of beta chain (S117V) | SEQ ID NO: 12 (wild-type (wt) beta chain) SEQ ID NO: 33 (substituted alpha chain), wherein Xaa at 116 is Ser, Xaa at 117 is Val, Xaa at 118 is Gly, and Xaa at 119 is Thr |
| a2-4 | Methionine substitution at position 117 of beta chain (S117M) | SEQ ID NO: 12 (wild-type (wt) beta chain) SEQ ID NO: 33 (substituted alpha chain), wherein Xaa at 116 is Ser, Xaa at 117 is Met, Xaa at 118 is Gly, and Xaa at 119 is Thr |

PBL from a human donor were untransduced or transduced with wild-type (wt) 6F9 TCR or one of each of the eight substituted TCRs. The cells were cultured alone (T cell only) or co-cultured with 624-CIITA, 526-CIITA, 1359-CIITA, H1299-CIITA, or 1764-CIITA. IFN-gamma secretion was measured. The results are set forth in FIG. 7. As shown in FIG. 7, the a 1, a2, and a 1-3 substituted TCRs demonstrated reactivity against CIITA-tumor cell lines.

EXAMPLE 9

This example demonstrates that substitution of the native constant region of the 6F9 TCR with a murine constant region increases the reactivity of the 6F9 TCR.

A TCR was prepared comprising the variable regions of the α and β chains of the wt 6F9 TCR and a murine constant region (6F9mC TCR) (SEQ ID NOs: 27 and 28).

The 6F9mC TCR demonstrated better MAGE-A3 tetramer and Vβ staining as compared to wt 6F9 TCR, as measured by flow cytometry. Without being bound to a particular theory, it is believed that the 6F9mC TCR provides improved pairing of the TCR α and β chains.

PBL from a human donor were untransduced or transduced with wt 6F9 TCR or 6F9mC TCR and cultured alone (T-cell only) or co-cultured with 624-CIITA, 1300-CIITA, 526-CIITA, 1359-CIITA, H1299-CIITA, 397-CIITA, 2630-CIITA, 2984-CIITA, 3071-CIITA, or 1764-CIITA cells. IFN-gamma secretion was measured. The results are shown in FIG. 8. As shown in FIG. 8, the 6F9mC-transduced cells showed a 2-5 fold increase in anti-tumor activity as compared to wt 6F9 TCR-transduced cells.

Untransduced cells, 6F9 TCR-transduced cells, or 6F9mC TCR-transduced cells were enriched for CD8 or CD4 and cultured alone (T-cell only) or co-cultured with 624-CIITA, SK37-CIITA, 526-CIITA, 1359-CIITA, H1299-CIITA, 397-CIITA, 2630-CIITA, 2984-CIITA, 3071-CIITA, or 1764-CIITA cells. Interferon-gamma secretion was measured. The results are shown in FIGS. 9A and 9B. As shown in FIGS. 9A and 9B, the CD8 and CD4 enriched 6F9mC-transduced cells maintained higher anti-tumor activity as compared to 6F9 TCR transduced cells for several cell lines, indicating high affinity of the 6F9mC TCR independent of co-receptors. The experiments were repeated using PBL from a second human donor and similar results were obtained. Comparisons of responses of CD4+ T cells transduced with the wild-type (Wt) 6F9 TCR with those of the cells transduced with the 6F9mc TCR indicated that the murine constant regions resulted in between two and five-fold enhancement in the response of transduced T cells against the seven MAGE-A3+ and HLA-DP*0401+ targets that were evaluated. In addition, the response of CD8+ T cells transduced with the 6F9mc were enhanced by between two and ten-fold above those seen in cells transduced with the wt 6F9 TCR. The responses of CD8+ T cells transduced with the 6F9mc were generally lower than CD4+ T cells transduced with this TCR, although comparable cytokine responses were observed in responses to some tumor targets.

EXAMPLE 10

This example demonstrates that upon tumor stimulation, 6F9mC TCR-transduced cells produce high levels of IFN-gamma and TNF-alpha and show a highly activated phenotype (as measured by increased 4-1BB, CD25, and CD69 expression).

Cells were CD4 or CD8 enriched and transduced with 6F9mC TCR. Transduced cells were co-cultured with tumor lines 624-CIITA, 2630-CIITA, 2984-CIITA, or Whitington-CIITA for 6 hours and then stained for intracellular IFN-gamma, interleukin (IL)-2, or tumor necrosis factor (TNF)-α. The 6F9mC TCR transduced cells showed specific intracellular IFN-gamma production upon tumor stimulation. The 6F9mC TCR transduced cells showed detectable IL-2 production and specific high TNF-α production upon tumor stimulation in the CD4-enriched fraction.

Cells were CD4 enriched and transduced with 6F9mC TCR. Transduced cells were co-cultured with tumor lines 624-CIITA, 2630-CIITA, 2984-CIITA, or Whitington-CIITA overnight and then stained for 4-1BB, CD25, and CD69. After overnight tumor stimulation, the majority of 6F9mC TCR-transduced cells expressed high levels of 4-1BB (indicative of antigen-specific activation), CD25, and CD69.

EXAMPLE 11

This example demonstrates that the 6F9 TCR mediates tumor cell recognition.

PBL were untransduced or transduced with wild-type 6F9 TCR and cultured alone or co-cultured with non-small cell lung cancer (NSCLC) cell line H11299 or melanoma cell line 526 mel, 624 mel, or 1359 mel. MAGE-A3 and DP*04 expression is shown in Table 8.

TABLE 8

| Cell line | MAGE-A3 | DP*04 |
|---|---|---|
| H1299 NSCLC | + | + |
| 526 mel | + | + |
| 624 mel | + | − |
| 1359 mel | + | − |

IFN-gamma expression was measured. The results are shown in FIG. 10B. As shown in FIG. 10B, the 6F9 TCR mediates tumor cell recognition.

EXAMPLE 12

This example demonstrates that the 6F9 and 6F9mc TCR possess a high degree of specificity for the MAGE-A3:$_{248-258}$ peptide.

In order to evaluate the fine specificity of antigen recognition mediated by cells transduced with the 6F9 and 6F9mc TCR, HLA-DP*0401+ target cells were pulsed with truncations of the MAGE-A3:$_{243-258}$ peptide or related peptides from MAGE family members. CD4+ T cells isolated from two patients' PBMC (PBMC-1 or PBMC-2) by negative selection were transduced with either the 6F9 TCR, the 6F9mc TCR, or were un-transduced and assayed 10 days following OKT3 stimulation for their response to 293-CIITA cells that were pulsed with 10 mg/ml of the peptides indicated in Table 9.

Analysis of the response to truncated MAGE-A3 peptides from two cultures of transduced CD4+ PBMC indicated that the 11-mer peptide QHFVQENYLEY (SEQ ID NO: 54) corresponding to amino acids 248-258 of the MAGE-A3 protein represented the minimal peptide that elicited a response comparable to that elicited by the MAGE-A3:$_{243-258}$ peptide (Table 9). The MAGE-A3:$_{243-258}$ peptide was predicted using an epitope prediction algorithm to possess a high affinity for HLA-DP*0401, and in addition, recognition of the truncated MAGE-A3 peptides appeared to correlate with T cell recognition (Table 9). Significant recognition was observed for the MAGE-A6:$_{248-258}$ peptide that contained a single substitution of tyrosine for histidine at position 249, but minimal reactivity was observed against additional members of the MAGE family of gene products that possessed between two and five differences from the MAGE-A3:$_{248-258}$ peptide. A BLAST search of the NCBI database revealed that the most closely related peptide was derived from the protein necdin. This peptide, which possessed five differences from the MAGE-A3:$_{248-258}$ peptide, was also not recognized by T cells transduced with the 6F9 or 6F9mc TCR. These findings indicate that the 6F9 TCR possesses a high degree of specificity for the MAGE-A3:$_{248-258}$ peptide, and suggest that T cells transduced with this TCR may possess little or no cross-reactivity with peptides derived from additional human proteins.

TABLE 9

| Gene (position) | SEQ ID NO: | Amino Acid Sequence | PBMC-1 transduced with: 6F9 | 6F9mc | None IFN-g (pg/ml) | PBMC-2 transduced with: 6F9 | 6F9mc | None | Predicted affinity (nM) |
|---|---|---|---|---|---|---|---|---|---|
| MAGE-A3: 243-258 | 2 | KKLLTQHFVQENYLEY | 10,220 | 15,210 | 33 | 10,350 | 17,520 | 45 | 3 |
| MAGE-A3: 243-256 | 47 | KKLLTQHFVQENYL | 1,018 | 1,815 | 72 | 1,670 | 2,490 | 78 | 323 |
| MAGE-A3: 243-255 | 48 | KKLLTQHFVQENY | 76 | 137 | 29 | 111 | 117 | 71 | 378 |
| MAGE-A3: 243-254 | 49 | KKLLTQHFVQEN | 28 | 0 | 67 | 30 | 39 | 78 | 466 |
| MAGE-A3: 243-253 | 50 | KKLLTQHFVQE | 0 | 40 | 38 | 30 | 45 | 90 | 2444 |
| MAGE-A3: 245-258 | 51 | LLTQHFVQENYLEY | 9,290 | 14,970 | 84 | 8,920 | 17,820 | 74 | 3 |
| MAGE-A3: 246-258 | 52 | LTQHFVQENYLEY | 7,140 | 12,700 | 56 | 9,200 | 16,170 | 76 | 3 |
| MAGE-A3: 247-258 | 53 | TQHFVQENYLEY | 6,710 | 10,600 | 30 | 6,810 | 13,280 | 41 | 3 |
| MAGE-A3: 248-258 | 54 | QHFVQENYLEY | 6,220 | 9,000 | 52 | 7,400 | 8,700 | 56 | 4 |
| MAGE-A3: 249-258 | 55 | HFVQENYLEY | 669 | 1,643 | 57 | 922 | 2,034 | 66 | 5 |
| MAGE-A6: 248-258 | 56 | QYFVQENYLEY | 6,440 | 11,800 | 54 | 13,200 | 8,370 | 127 | 3 |
| MAGE-A2/A12: 248-258 | 57 | QDLVQENYLEY | 33 | 66 | 49 | 37 | 56 | 65 | 59 |
| MAGE-A4/A9: 249-259 | 58 | QDWVQENYLEY | 0 | 23 | 32 | 22 | 26 | 62 | 92 |
| MAGE-A8: 251-261 | 59 | QEWVQENYLEY | 43 | 58 | 79 | 39 | 41 | 55 | 87 |
| MAGE-A1/B4: 241-251 | 60 | QDLVQEKYLEY | 129 | 126 | 55 | 108 | 84 | 53 | 16 |
| MAGE-B2: 250-260 | 61 | KDLVQEKYLEY | 0 | 0 | 43 | 7 | 20 | 38 | 16 |
| MAGE-B10: 250-260 | 62 | KDLVKENYLEY | 22 | 18 | 69 | 28 | 34 | 66 | 105 |
| MAGE-B16: 252-262 | 63 | KDFVKEKYLEY | 0 | 27 | 16 | 11 | 28 | 42 | 3 |
| MAGE-C1: 113-123 | 64 | KVWVQEHYLEY | 9 | 0 | 30 | 25 | 27 | 30 | 35 |
| MAGE-D4: 300-315 | 65 | RKLITDDFVKQKYLEY | 193 | 234 | 81 | 194 | 268 | 80 | 6 |
| MAGE-D2: 413-428 | 66 | KKLITDEFVKQKYLDY | 82 | 43 | 56 | 226 | 223 | 71 | 8 |
| MAGE-L2: 582-597 | 67 | KKLITEVFVRQKYLEY | 45 | 56 | 58 | 78 | 107 | 114 | 6 |
| MAGE-G1: 220-235 | 68 | KKLITEDFVRQRYLEY | 0 | 29 | 68 | 25 | 33 | 62 | 3 |
| Necdin: 237-247 | 69 | EEFVQMNYLKY | 0 | 22 | 59 | 21 | 32 | 83 | 13 |
| No peptide | | | 0 | 5 | 58 | 15 | 25 | 59 | |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified nucleic acid comprising a nucleotide sequence encoding a T-cell receptor (TCR) having antigenic specificity for MAGE-A3$_{243\text{-}258}$ and MAGE-A6, wherein the TCR comprises:
   (a) SEQ ID NOs: 3, 4, 6, 7,
      (i) SEQ ID NO: 29, wherein:
         Xaa4 is Ser, Ala, Leu, Ile, Val, or Met;
         Xaa5 is Ser, Ala, Leu, Ile, Val, or Met;
         Xaa6 is Gly, Ala, Leu, Ile, Val, or Met; and
         Xaa7 is Thr, Ala, Leu, Ile, Val, or Met; and
      (ii) SEQ ID NO: 30, wherein:
         Xaa4 is Arg, Ala, Leu, Ile, Val, or Met;
         Xaa5 is Thr, Ala, Leu, Ile, Val, or Met;
         Xaa6 is Gly, Ala, Leu, Ile, Val, or Met; and
         Xaa7 is Pro, Ala, Leu, Ile, Val, or Met; or
   (b) SEQ ID NOs: 3-8.

2. An isolated or purified nucleic acid comprising a nucleotide sequence encoding a TCR comprising:
   (a) SEQ ID NOs: 3-8,
   (b) SEQ ID NOs: 21-22, or
   (c) (i) SEQ ID NO: 29, wherein:
         Xaa4 is Ser, Ala, Leu, Ile, Val, or Met;
         Xaa5 is Ser, Ala, Leu, Ile, Val, or Met;
         Xaa6 is Gly, Ala, Leu, Ile, Val, or Met; and
         Xaa7 is Thr, Ala, Leu, Ile, Val, or Met;
      (ii) SEQ ID NO: 30, wherein:
         Xaa4 is Arg, Ala, Leu, Ile, Val, or Met;
         Xaa5 is Thr, Ala, Leu, Ile, Val, or Met;
         Xaa6 is Gly, Ala, Leu, Ile, Val, or Met; and
         Xaa7 is Pro, Ala, Leu, Ile, Val, or Met; and
   (iii) SEQ ID NOs: 3, 4, 6, and 7,
         wherein the TCR has antigenic specificity for MAGE-A3 in the context of HLA-DPβ1*04.

3. The isolated or purified nucleic acid according to claim 2, wherein the TCR comprises:
   (i) SEQ ID NO: 29, wherein:
      Xaa4 is Ser, Ala, Leu, Ile, Val, or Met;
      Xaa5 is Ser, Ala, Leu, Ile, Val, or Met;
      Xaa6 is Gly, Ala, Leu, Ile, Val, or Met; and
      Xaa7 is Thr, Ala, Leu, Ile, Val, or Met;
   (ii) SEQ ID NO: 30, wherein:
      Xaa4 is Arg, Ala, Leu, Ile, Val, or Met;
      Xaa5 is Thr, Ala, Leu, Ile, Val, or Met;

Xaa6 is Gly, Ala, Leu, Ile, Val, or Met; and
Xaa7 is Pro, Ala, Leu, Ile, Val, or Met; and
(iii) SEQ ID NOs: 3, 4, 6, and 7.

4. The nucleic acid according to claim 3, wherein the TCR comprises (a) SEQ ID NO: 29, wherein Xaa4 is Ala, Xaa5 is Ser, Xaa6 is Gly, and Xaa7 is Thr, or (b) SEQ ID NO: 29, wherein Xaa4 is Ser, Xaa5 is Ala, Xaa6 is Gly, and Xaa7 is Thr.

5. The isolated or purified nucleic acid according to claim 1, wherein the TCR comprises a murine constant region.

6. The isolated or purified nucleic acid according to claim 5, wherein the TCR comprises a murine constant region comprising SEQ ID NO: 25 and/or SEQ ID NO: 26.

7. The isolated or purified nucleic acid according to claim 1, wherein the TCR comprises:
   a first amino acid sequence selected from the group consisting of:
      (i) SEQ ID NO: 31, wherein:
         Xaa116 is Ser, Ala, Leu, Ile, Val, or Met;
         Xaa117 is Ser, Ala, Leu, Ile, Val, or Met;
         Xaa118 is Gly, Ala, Leu, Ile, Val, or Met; and
         Xaa119 is Thr, Ala, Leu, Ile, Val, or Met; and
      (ii) SEQ ID NO: 9;
   and a second amino acid sequence selected from the group consisting of:
      (i) SEQ ID NO: 32, wherein:
         Xaa115 is Arg, Ala, Leu, Ile, Val, or Met;
         Xaa116 is Thr, Ala, Leu, Ile, Val, or Met;
         Xaa117 is Gly, Ala, Leu, Ile, Val, or Met; and
         Xaa118 is Pro, Ala, Leu, Ile, Val, or Met; and
      (ii) SEQ ID NO: 10.

8. The nucleic acid according to claim 7, wherein the TCR comprises:
   (a) SEQ ID NO: 31, wherein Xaa116 is Ala, Xaa117 is Ser, Xaa118 is Gly, and Xaal119 is Thr, or
   (b) SEQ ID NO: 31, wherein Xaa116 is Ser, Xaa117 is Ala, Xaa118 is Gly, and Xaal119 is Thr.

9. The isolated or purified nucleic acid according to claim 2, wherein the TCR comprises:
   a first amino acid sequence selected from the group consisting of:
      (i) SEQ ID NO: 33, wherein:
         Xaa116 is Ser, Ala, Leu, Ile, Val, or Met;
         Xaa117 is Ser, Ala, Leu, Ile, Val, or Met;
         Xaa118 is Gly, Ala, Leu, Ile, Val, or Met; and
         Xaa119 is Thr, Ala, Leu, Ile, Val, or Met;
      (ii) SEQ ID NO: 11;
      (iii) SEQ ID NO: 21; and
      (iv) SEQ ID NO: 27;
   and a second amino acid sequence selected from the group consisting of:
      (i) SEQ ID NO: 34, wherein:
         Xaa115 is Arg, Ala, Leu, Ile, Val, or Met;
         Xaa116 is Thr, Ala, Leu, Ile, Val, or Met;
         Xaa117 is Gly, Ala, Leu, Ile, Val, or Met; and
         Xaa118 is Pro, Ala, Leu, Ile, Val, or Met;
      (ii) SEQ ID NO: 12;
      (iii) SEQ ID NO: 22; and
      (iv) SEQ ID NO: 28.

10. The nucleic acid according to claim 9, wherein the TCR comprises:
    (a) SEQ ID NO: 33, wherein Xaa116 is Ala, Xaa117 is Ser, Xaa118 is Gly, and Xaa119 is Thr, or
    (b) SEQ ID NO: 33, wherein Xaa116 is Ser, Xaa117 is Ala, Xaa118 is Gly, and Xaa119 is Thr.

11. An isolated or purified nucleic acid comprising a nucleotide sequence encoding a polypeptide comprising a functional portion of the TCR of claim 1, wherein the functional portion comprises:
    (a) SEQ ID NOs: 3, 4, 6, 7,
       (i) SEQ ID NO: 29, wherein:
          Xaa4 is Ser, Ala, Leu, Ile, Val, or Met;
          Xaa5 is Ser, Ala, Leu, Ile, Val, or Met;
          Xaa6 is Gly, Ala, Leu, Ile, Val, or Met; and
          Xaa7 is Thr, Ala, Leu, Ile, Val, or Met; and
       (ii) SEQ ID NO: 30, wherein:
          Xaa4 is Arg, Ala, Leu, Ile, Val, or Met;
          Xaa5 is Thr, Ala, Leu, Ile, Val, or Met;
          Xaa6 is Gly, Ala, Leu, Ile, Val, or Met; and
          Xaa7 is Pro, Ala, Leu, Ile, Val, or Met; or
    (b) SEQ ID NOs: 3-8.

12. The isolated or purified nucleic acid of claim 11, wherein the functional portion comprises:
    (a) SEQ ID NO: 29, wherein Xaa4 is Ala, Xaa5 is Ser, Xaa6 is Gly, and Xaa7 is Thr, or
    (b) SEQ ID NO: 29, wherein Xaa4 is Ser, Xaa5 is Ala, Xaa6 is Gly, and Xaa7 is Thr.

13. The isolated or purified nucleic acid of claim 11, wherein the portion comprises:
    a first amino acid sequence selected from the group consisting of:
       (i) SEQ ID NO: 31, wherein:
          Xaa116 is Ser, Ala, Leu, Ile, Val, or Met;
          Xaa117 is Ser, Ala, Leu, Ile, Val, or Met;
          Xaa118 is Gly, Ala, Leu, Ile, Val, or Met; and
          Xaa119 is Thr, Ala, Leu, Ile, Val, or Met; and
       (ii) SEQ ID NO: 9;
    and a second amino acid sequence selected from the group consisting of:
       (i) SEQ ID NO: 32, wherein:
          Xaa115 is Arg, Ala, Leu, Ile, Val, or Met;
          Xaa116 is Thr, Ala, Leu, Ile, Val, or Met;
          Xaa117 is Gly, Ala, Leu, Ile, Val, or Met; and
          Xaa118 is Pro, Ala, Leu, Ile, Val, or Met; and
       (ii) SEQ ID NO: 10.

14. The isolated or purified nucleic acid of claim 13, wherein the portion comprises:
    (a) SEQ ID NO:31, wherein Xaa116 is Ala, Xaa117 is Ser, Xaa118 is Gly, and Xaa119 is Thr, or
    (b) SEQ ID NO: 31, wherein Xaa116 is Ser, Xaa117 is Ala, Xaa118 is Gly, and Xaa119 is Thr.

15. An isolated or purified nucleic acid comprising a nucleotide sequence encoding a polypeptide comprising a functional portion of the TCR of claim 2, wherein the portion comprises:
    a first amino acid sequence selected from the group consisting of:
       (i) SEQ ID NO: 33, wherein:
          Xaa116 is Ser, Ala, Leu, Ile, Val, or Met;
          Xaa117 is Ser, Ala, Leu, Ile, Val, or Met;
          Xaa118 is Gly, Ala, Leu, Ile, Val, or Met; and
          Xaa119 is Thr, Ala, Leu, Ile, Val, or Met;
       (ii) SEQ ID NO: 11;
       (iii) SEQ ID NO: 21; and
       (iv) SEQ ID NO: 27;
    and a second amino acid sequence selected from the group consisting of:
       (i) SEQ ID NO: 34, wherein:
          Xaa115 is Arg, Ala, Leu, Ile, Val, or Met;
          Xaa116 is Thr, Ala, Leu, Ile, Val, or Met;
          Xaa117 is Gly, Ala, Leu, Ile, Val, or Met; and
          Xaa118 is Pro, Ala, Leu, Ile, Val, or Met;

(ii) SEQ ID NO: 12;
(iii) SEQ ID NO: 22; and
(iv) SEQ ID NO: 28.

16. The isolated or purified nucleic acid of claim 15, wherein the portion comprises:
(a) SEQ ID NO: 33, wherein Xaa116 is Ala, Xaa117 is Ser, Xaa118 is Gly, and Xaa119 is Thr, or
(b) SEQ ID NO: 33, wherein Xaa116 is Ser, Xaa117 is Ala, Xaa118 is Gly, and Xaa119 is Thr.

17. An isolated or purified nucleic acid comprising a nucleotide sequence encoding a protein comprising at least one of the polypeptides of claim 11.

18. An isolated or purified nucleic acid comprising a nucleotide sequence encoding a protein comprising a functional portion of the TCR according to claim 1, comprising a first polypeptide chain comprising:
(a) SEQ ID NO: 3-5; or
(b) SEQ ID NOs: 3, 4, and SEQ ID NO: 29, wherein:
Xaa4 is Ser, Ala, Leu, Ile, Val, or Met;
Xaa5 is Ser, Ala, Leu, Ile, Val, or Met;
Xaa6 is Gly, Ala, Leu, Ile, Val, or Met; and
Xaa7 is Thr, Ala, Leu, Ile, Val, or Met;
and a second polypeptide chain comprising:
(a) SEQ ID NOs: 6-8; or
(b) SEQ ID NOs: 6, 7, and SEQ ID NO: 30, wherein:
Xaa4 is Arg, AlHa, Leu, Ile, Val, or Met;
Xaa5 is Thr, Ala, Leu, Ile, Val, or Met;
Xaa6 is Gly, Ala, Leu, Ile, Val, or Met; and
Xaa7 is Pro, Ala, Leu, Ile, Val, or Met.

19. The nucleic acid of claim 18, wherein the first polypeptide chain comprises:
(a) SEQ ID NO: 29, wherein Xaa4 is Ala, Xaa5 is Ser, Xaa6 is Gly, and Xaa7 is Thr, or
(b) SEQ ID NO: 29, wherein Xaa4 is Ser, Xaa5 is Ala, Xaa6 is Gly, and Xaa7 is Thr.

20. The isolated or purified nucleic acid according to claim 18, wherein the protein comprises a first polypeptide chain comprising an amino acid sequence selected from the group consisting of:
(i) SEQ ID NO: 31, wherein:
Xaa116 is Ser, Ala, Leu, Ile, Val, or Met;
Xaa117 is Ser, Ala, Leu, Ile, Val, or Met;
Xaa118 is Gly, Ala, Leu, Ile, Val, or Met; and
Xaa119 is Thr, Ala, Leu, Ile, Val, or Met; and
(ii) SEQ ID NO:9;
and a second polypeptide chain comprising an amino acid sequence selected from the group consisting of:
(i) SEQ ID NO: 32, wherein:
Xaa115 is Arg, Ala, Leu, Ile, Val, or Met;
Xaa116 is Thr, Ala, Leu, Ile, Val, or Met;
Xaa117 is Gly, Ala, Leu, Ile, Val, or Met; and
Xaa118 is Pro, Ala, Leu, Ile, Val, or Met;
and (ii) SEQ ID NO: 10.

21. The nucleic acid of claim 20, wherein the first polypeptide chain comprises:
(a) SEQ ID NO: 31, wherein Xaa116 is Ala, Xaa117 is Ser, Xaa118 is Gly, and Xaa119 is Thr, or
(b) SEQ ID NO: 31, wherein Xaa116 is Ser, Xaa117 is Ala, Xaa118 is Gly, and Xaa119 is Thr.

22. An isolated or purified nucleic acid comprising a nucleotide sequence encoding a protein comprising a first polypeptide chain comprising an amino acid sequence selected from the group consisting of:
(i) SEQ ID NO: 33, wherein:
Xaa116 is Ser, Ala, Leu, Ile, Val, or Met;
Xaa117 is Ser, Ala, Leu, Ile, Val, or Met;
Xaa118 is Gly, Ala, Leu, Ile, Val, or Met; and
Xaa119 is Thr, Ala, Leu, Ile, Val, or Met;
(ii) SEQ ID NO: 11;
(iii) SEQ ID NO: 21; and
(iv) SEQ ID NO: 27;
and a second polypeptide chain comprising an amino acid sequence selected from the group consisting of:
(i) SEQ ID NO: 34, wherein:
Xaa115 is Arg, Ala, Leu, Ile, Val, or Met;
Xaa116 is Thr, Ala, Leu, Ile, Val, or Met;
Xaa117 is Gly, Ala, Leu, Ile, Val, or Met; and
Xaa118 is Pro, Ala, Leu, Ile, Val, or Met;
(ii) SEQ ID NO: 12;
(iii) SEQ ID NO: 22; and
(iv) SEQ ID NO: 28.

23. The nucleic acid of claim 22, wherein the first polypeptide chain comprises:
(a) SEQ ID NO: 33, wherein Xaa116 is Ala, Xaa117 is Ser, Xaa118 is Gly, and Xaa119 is Thr, or
(b) SEQ ID NO: 33, wherein Xaa116 is Ser, Xaa117 is Ala, Xaa118 is Gly, and Xaal 119 is Thr.

24. The isolated or purified nucleic acid of claim 17, wherein the protein is a fusion protein.

25. The isolated or purified nucleic acid of claim 17, wherein the protein is a recombinant antibody.

26. The isolated or purified nucleic acid according to claim 2, wherein the nucleotide sequence comprises a nucleotide sequence selected from the group consisting of SEQ ID NOs: 37-44.

27. A recombinant expression vector comprising the nucleic acid according to claim 1.

28. An isolated host cell comprising the recombinant expression vector of claim 27.

29. The host cell according to claim 28, wherein the cell is human.

30. A population of cells comprising at least one host cell of claim 28.

31. A pharmaceutical composition comprising the population of cells according to claim 30 and a pharmaceutically acceptable carrier.

32. A method of detecting the presence of cancer in a mammal, comprising:
(a) contacting a sample comprising one or more cells from the mammal with the population of cells according to claim 30, thereby forming a complex, and
(b) detecting the complex, wherein detection of the complex is indicative of the presence of cancer in the mammal, wherein the cancer expresses MAGE-A3 and/or MAGE-A6.

33. The method of claim 32, wherein the cancer is melanoma, breast cancer, lung cancer, prostate cancer, synovial cell sarcoma, head and neck cancer, esophageal cancer, or ovarian cancer.

34. A method of treating cancer in a mammal, the method comprising administering to the mammal the population of cells of claim 30 in an amount effective to treat cancer in the mammal, wherein the cancer expresses MAGE-A3 and/or MAGE-A6.

35. The method according to claim 34, wherein the cancer is melanoma, breast cancer, lung cancer, prostate cancer, synovial cell sarcoma, head and neck cancer, esophageal cancer, or ovarian cancer.

* * * * *

UNITED STATES PATENT AND TRADEMARK OFFICE
CERTIFICATE OF CORRECTION

PATENT NO. : 9,879,065 B2
APPLICATION NO. : 14/427671
DATED : January 30, 2018
INVENTOR(S) : Paul F. Robbins, Steven A. Rosenberg and Xin Yao It is certified that error appears in the above-identified patent and that said Letters Patent is hereby corrected as shown below:

In the Claims

Claim 18, Column 91, Line 25, change "Xaa4 is Arg, AlHa, Leu, Ile, Val, or Met;" to
-- Xaa4 is Arg, Ala, Leu, Ile, Val, or Met; --

Claim 23, Column 92, Line 21, change "Xaal 119 is Thr" to -- Xaa119 is Thr --

Signed and Sealed this
Twenty-fifth Day of September, 2018

Andrei Iancu
*Director of the United States Patent and Trademark Office*